(12) United States Patent
Zahler et al.

(10) Patent No.: US 9,573,918 B2
(45) Date of Patent: Feb. 21, 2017

(54) FUMIGILLOL COMPOUNDS AND METHODS OF MAKING AND USING SAME

(71) Applicant: Zafgen, Inc., Cambridge, MA (US)

(72) Inventors: Robert Zahler, Pennington, NJ (US); James E. Vath, Lynnfield, MA (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 14/399,392

(22) PCT Filed: May 8, 2013

(86) PCT No.: PCT/US2013/040080
§ 371 (c)(1),
(2) Date: Nov. 6, 2014

(87) PCT Pub. No.: WO2013/169860
PCT Pub. Date: Nov. 14, 2013

(65) Prior Publication Data
US 2015/0126489 A1    May 7, 2015

Related U.S. Application Data

(60) Provisional application No. 61/644,612, filed on May 9, 2012.

(51) Int. Cl.
| C07D 303/40 | (2006.01) |
| C07D 405/12 | (2006.01) |
| C07D 303/31 | (2006.01) |
| C07D 303/46 | (2006.01) |
| C07D 405/14 | (2006.01) |

(52) U.S. Cl.
CPC ............ *C07D 303/40* (2013.01); *C07D 303/31* (2013.01); *C07D 303/46* (2013.01); *C07D 405/12* (2013.01); *C07D 405/14* (2013.01)

(58) Field of Classification Search
CPC ... C07D 303/31; C07D 303/40; C07D 303/46; C07D 405/12; C07D 405/14
See application file for complete search history.

(56) References Cited

U.S. PATENT DOCUMENTS

| | | | |
|---|---|---|---|
| 5,164,410 A | 11/1992 | Kishimoto et al. | |
| 5,166,172 A | 11/1992 | Kishimoto et al. | |
| 5,180,735 A | 1/1993 | Kishimoto et al. | |
| 5,180,738 A | 1/1993 | Kishimoto et al. | |
| 5,196,406 A | 3/1993 | Kamei et al. | |
| 5,204,345 A * | 4/1993 | Kishimoto ............ | C07D 405/12 514/231.5 |
| 5,288,722 A | 2/1994 | Kishimoto et al. | |
| 5,290,807 A | 3/1994 | Folkman et al. | |
| 5,422,363 A | 6/1995 | Yanai et al. | |
| 5,536,623 A | 7/1996 | Ohmachi et al. | |
| 5,698,586 A | 12/1997 | Kishimoto et al. | |
| 5,767,293 A * | 6/1998 | Oku .................... | C07D 303/22 514/231.5 |
| 5,789,405 A * | 8/1998 | Oku .................... | C07D 303/22 514/227.8 |
| 5,846,562 A | 12/1998 | Yanai et al. | |
| 5,900,431 A | 5/1999 | Molina et al. | |
| 6,017,949 A | 1/2000 | D'Amato et al. | |
| 6,017,954 A | 1/2000 | Folkman et al. | |
| 6,040,337 A | 3/2000 | Hong, II et al. | |
| 6,063,812 A | 5/2000 | Hong et al. | |
| 6,180,626 B1 | 1/2001 | Shimomura et al. | |
| 6,207,704 B1 | 3/2001 | Liu et al. | |
| 6,242,494 B1 | 6/2001 | Craig et al. | |
| 6,277,391 B1 | 8/2001 | Seo et al. | |
| 6,306,819 B1 | 10/2001 | Rupnick et al. | |
| 6,323,228 B1 | 11/2001 | BaMaung et al. | |
| 6,383,471 B1 | 5/2002 | Chen et al. | |
| 6,548,477 B1 | 4/2003 | Olson et al. | |
| 6,566,541 B2 | 5/2003 | Liu et al. | |
| 6,664,244 B1 | 12/2003 | Furuse et al. | |
| 6,803,382 B2 | 10/2004 | Eustache et al. | |
| 6,877,863 B2 | 4/2005 | Wood et al. | |
| 6,989,392 B2 | 1/2006 | Collins et al. | |
| 7,030,262 B2 | 4/2006 | BaMaung et al. | |
| 7,037,890 B2 | 5/2006 | Olson et al. | |
| 7,084,108 B2 | 8/2006 | Olson et al. | |
| 7,268,111 B2 | 9/2007 | Olson et al. | |
| 7,304,082 B2 | 12/2007 | Marino, Jr. et al. | |
| 7,718,695 B2 | 5/2010 | Kim et al. | |
| 8,367,721 B2 | 2/2013 | Hughes et al. | |
| 8,642,650 B2 | 2/2014 | Hughes et al. | |
| 8,980,946 B2 | 3/2015 | Hughes | |

(Continued)

FOREIGN PATENT DOCUMENTS

| EP | 0682020 A1 | 11/1995 |
| WO | WO-98/56372 A1 | 12/1998 |

(Continued)

OTHER PUBLICATIONS

Kerns, Edward et al, Drug-like Properties: Concepts, Structure Design and Methods: from ADME to Toxicity Optimization (Elsevier, 2008) pp. 92-93.*
Goosen et al., Pharmaceutical Research vol. 19, No. 1, 13-19 (Jan. 2002).*
Fourie, International Journal of Pharmaceutics vol. 279, Issues 1-2, Jul. 26, 2004, pp. 59-66.*
Edwards, J. Med. Chem. 39 (1996), pp. 1112-1124, or Rautio, Eur. J. Pharm. Sci. 11:157-163 (2000).*
Rautio, Eur. J. Pharm. Sci. 11:157-163 (2000).*
U.S. Appl. No. 15/068,942, Oxaspiro[2.5]Octane Derivatives and Analogs, filed Mar. 14, 2016.
U.S. Appl. No. 14/856,929, Treatment of Obesity Using Non-Daily Administration of 6-O(4-Dimethylaminoethyoxy) Cinnamoyl Fumagillol, filed Sep. 17, 2015.
Anderson, "The Use of Fumagillin in Amoebiasis," Annals of the New York Academy of Sciences, 55:1118-1124, 1952.
Benny et al., "An Orally Delivered Small-Molecule Formulation with Antiangiogenic and Anticancer Activity," Nat Biotechnol. Jul. 2008;26(7):799-807.

(Continued)

*Primary Examiner* — Valerie Rodriguez-Garcia
(74) *Attorney, Agent, or Firm* — Goodwin Procter LLP

(57) ABSTRACT

The disclosure provides fumagillol type compounds and their use in treating medical disorders, such as obesity. Pharmaceutical compositions and methods of using, e.g. in the treatment of obesity are provided.

17 Claims, 6 Drawing Sheets

(56) References Cited

U.S. PATENT DOCUMENTS

| | | | |
|---|---|---|---|
| 9,000,035 | B2 | 4/2015 | Hughes |
| 9,173,865 | B2 | 11/2015 | Hughes |
| 9,328,082 | B2 | 5/2016 | Vath et al. |
| 2003/0220371 | A1 | 11/2003 | Kallander et al. |
| 2004/0067266 | A1 | 4/2004 | Toppo |
| 2004/0116495 | A1 | 6/2004 | Marino, Jr. et al. |
| 2004/0157836 | A1 | 8/2004 | Comess et al. |
| 2004/0167128 | A1 | 8/2004 | Comess et al. |
| 2004/0204472 | A1 | 10/2004 | Briggs et al. |
| 2005/0037994 | A1 | 2/2005 | Kim et al. |
| 2005/0239878 | A1 | 10/2005 | Thompson et al. |
| 2006/0045865 | A1 | 3/2006 | Jacob et al. |
| 2006/0069161 | A1 | 3/2006 | Lee et al. |
| 2006/0276512 | A1 | 12/2006 | Han et al. |
| 2007/0078172 | A1 | 4/2007 | McElroy et al. |
| 2008/0200402 | A1 | 8/2008 | Alvinerie et al. |
| 2009/0148396 | A1 | 6/2009 | Akullian et al. |
| 2010/0016425 | A1 | 1/2010 | Vath |
| 2010/0111894 | A1 | 5/2010 | Benny-Ratsaby et al. |
| 2012/0004162 | A1 | 1/2012 | Vath |
| 2012/0010259 | A1 | 1/2012 | Vath |
| 2012/0010290 | A1 | 1/2012 | Vath |
| 2012/0034233 | A1 | 2/2012 | Hughes et al. |
| 2012/0322867 | A1 | 12/2012 | Hughes et al. |
| 2013/0316994 | A1 | 11/2013 | Hughes |
| 2014/0011870 | A1 | 1/2014 | Hughes |
| 2014/0045934 | A1 | 2/2014 | Hughes |
| 2014/0045935 | A1 | 2/2014 | Hughes |
| 2014/0051752 | A1 | 2/2014 | Hughes |
| 2014/0336251 | A1 | 11/2014 | Hughes et al. |
| 2015/0150840 | A1 | 6/2015 | Vath |
| 2015/0150857 | A1 | 6/2015 | Vath |
| 2015/0209320 | A1 | 7/2015 | Hughes et al. |
| 2015/0209321 | A1 | 7/2015 | Hughes |
| 2015/0335608 | A1 | 11/2015 | Hughes et al. |
| 2015/0361061 | A1 | 12/2015 | Vath |

FOREIGN PATENT DOCUMENTS

| | | | |
|---|---|---|---|
| WO | WO-99/39702 | A2 | 8/1999 |
| WO | WO-99/57097 | A2 | 11/1999 |
| WO | WO-99/59986 | A1 | 11/1999 |
| WO | WO-99/59987 | A1 | 11/1999 |
| WO | WO-00/64876 | A1 | 11/2000 |
| WO | WO-02/26782 | A2 | 4/2002 |
| WO | WO-02/42295 | A2 | 5/2002 |
| WO | WO-02/083065 | A2 | 10/2002 |
| WO | WO-03/027104 | A1 | 4/2003 |
| WO | WO-03/082845 | A1 | 10/2003 |
| WO | WO-2004/033419 | A1 | 4/2004 |
| WO | WO-2005/066197 | A2 | 7/2005 |
| WO | WO-2005/082349 | A1 | 9/2005 |
| WO | WO-2006/010498 | A2 | 2/2006 |
| WO | WO-2006/080591 | A1 | 8/2006 |
| WO | WO-2009/073445 | A2 | 6/2009 |
| WO | WO-2010/042163 | A2 | 4/2010 |
| WO | WO-2010/048499 | A1 | 4/2010 |
| WO | WO-2010/065877 | A2 | 6/2010 |
| WO | WO-2010/065879 | A2 | 6/2010 |
| WO | WO-2010/065881 | A2 | 6/2010 |
| WO | WO 2010/065883 | * | 6/2010 |
| WO | WO-2010/065883 | A2 | 6/2010 |
| WO | WO-2011/044506 | A2 | 4/2011 |
| WO | WO-2011/085198 | A1 | 7/2011 |
| WO | WO-2011/085201 | A1 | 7/2011 |
| WO | WO-2011/088055 | A2 | 7/2011 |
| WO | WO-2011/127304 | A2 | 10/2011 |
| WO | WO-2011/150338 | A1 | 12/2011 |
| WO | WO-2012/012642 | A1 | 1/2012 |
| WO | WO-2012/064838 | A1 | 3/2012 |
| WO | WO-2012/051318 | A1 | 4/2012 |
| WO | WO-2012/064928 | A1 | 5/2012 |
| WO | WO-2012/074968 | A1 | 6/2012 |
| WO | WO-2012/075020 | A1 | 6/2012 |
| WO | WO-2012/075026 | A1 | 6/2012 |
| WO | WO-2012/103333 | A1 | 8/2012 |
| WO | WO-2012/122264 | A1 | 9/2012 |
| WO | WO-2012/154676 | A1 | 11/2012 |
| WO | WO-2012/154678 | A1 | 11/2012 |
| WO | WO-2012/154679 | A1 | 11/2012 |
| WO | WO-2013/033430 | A1 | 3/2013 |
| WO | WO-2013/055385 | A2 | 4/2013 |
| WO | WO-2013/109735 | A1 | 7/2013 |
| WO | WO-2013/109739 | A1 | 7/2013 |
| WO | WO-2013/169727 | A1 | 11/2013 |
| WO | WO-2013/169860 | A1 | 11/2013 |

OTHER PUBLICATIONS

Bernier et al.,"Fumagillin class inhibitors of methionine aminopeptidase-2," Drugs of the Future 30(5):497-500, 2005.

Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.

Braunwald et al., "Obesity" in Harrison's Principles of Internal Medicine, 15th Ed., McGraw Hill (New York) pp. 479-486, 2001.

Butler et al., "Clinical Findings and Natural History of Prader-Willi Syndrome," Chapter 1; Clinical Findings and Natural History of PWS, pp. 3-48 (2006).

Cassidy et al., "Prader-Willi syndrome," European Journal of Human Genetics 17:3-13 (2009).

Cassidy et al., "Prader-Willi syndrome," Genetics in Medicine, vol. 14(1) pp. 10-26 (2012).

Cataletto et al., "Prader-Willi syndrome: A primer for clinicians," International Journal of Pediatric Endocrinology, vol. 12:1-13 (2011).

Chun et al., "Novel inhibitors targeted to methionine aminopeptidase 2 (MetAP2) strongly inhibit the growth of cancers in xenografted nude model," Int J Cancer. Mar. 10, 2005;114(1):124-30.

Didier et al., "Antimicrosporidial Activities of Fumagillin, TNP-470, Ovalicin, and Ovalicin Derivatives in Vitro and in Vivo" Antimicrob Agents Chemother. Jun. 2006;50(6):2146-55.

DiPaolo et al.,"Studies on the Carcinolytic Activity of Fumagillin and Some of its Derivatives," Antibiot Annu.1958-1959;6:541-6.

Drevs et al.,"Antiangiogenic Potency of FK866/K22.175, a New Inhibitor of Intracellular NAD Biosynthesis, in Murine Renal Cell Carcinoma," Anticancer Res. Nov.-Dec. 2003;23(6C):4853-4858.

Dumas et al., "Synthesis and Structure Activity Relationships of Novel Small Molecule Cathepsin D Inhibitors" Bioorg Med Chem Lett. Sep. 6, 1999;9(17):2531-6.

Dykens et al., "Assessment of Hyperphagia in Prader-Willi Syndrome," Obesity 15:7 (2007).

Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.").

Edgar et al., "Body composition in Prader-Willi syndrome compared with nonsyndromal obesity: Relationship to physical activity and growth homrone function," The Journal of Pediatrics 139:5, 708-714 (2001).

Einfield et al., "Mortality in Prader-Willi Syndrome," Am. J. Ment. Retard. 111(3):193-198 (2006).

European Communication for EP Application No. 12 798 444.1, dated Aug. 28, 2015 (8 pages).

European Search Report for EP 09798793 dated Oct. 11, 2011, 9 pages.

Evdokimov et al., "Serendipitious discovery of novel bacterial methionine aminopeptidase inhibitors," Proteins Feb. 15; 66(3):538-546 (2007).

Everhart, "Contributions of Obesity and Weight Loss to Gallstone Disease" Ann Intern Med. Nov. 15, 1993;119(10):1029-35.

Garrabrant et al.,"Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.

Garrison et al., "A metabolic basis for fibromyalgia and its related disorders: the possible role of resistance to thyroid hormone," Med. Hypotheses. Aug.;61(2):182-189 (2003).

(56) References Cited

OTHER PUBLICATIONS

Han et al., "Design and Synthesis of Highly Potent Fumagillin Analogues from Homology Modeling for a Human MetAP-2," Bioorg Med Chem Lett. Jan. 3, 2000;10(1):39-43.
Holland et al., "The paradox of Prader-Willi syndrome: a genetic model of starvation," The Lancet 362, 989-991 (2003).
Huang et al., "Inhibition of Monometalated Methionine Aminopeptidase: Inhibitor Discovery and Crystallographic Analysis," J. Med. Chem., Nov. 15;50(23):5735-5742 (2007).
Ingber et al., "Synthetic Analogues of Fumagillin that Inhibit Angiogenesis and Suppress Tumour Growth," Nature, 348(6301):555-557 (1990).
International Search Report for International Application No. PCT/US2011/020515, International Filing Date Jul. 1, 2011, 4 pages.
International Search Report for International Application No. PCT/US2011/020866, mailed Jul. 22, 2011, 8 pages.
International Search Report for International Application No. PCT/US2011/060127, mailed Jan. 2, 2012, 2 pages.
International Search Report for International Application No. PCT/US2011/062320, mailed Feb. 17, 2012, 3 pages.
International Search Report for International Application No. PCT/US2011/062421, mailed Feb. 17, 2012, 3 pages.
International Search Report for International Application No. PCT/US2011/38352, International Filing Date May 27, 2011,3 pages.
International Search Report for International Application No. PCT/US2012/000461, mailed May 2, 2013, 7 pages.
International Search Report for International Application PCT/US2010/052050, dated Mar. 25, 2011, 3 pages.
Jauregi et al., "Behavioral profile of adults with Prader-Willi syndrome: correlations with individual and environmental variables," Journal of Neurodevelopmental Disorders 5:18, 1-10 (2013).
Jeong et al, "Total synthesis and antiangiogenic activity of cyclopentane analogues of fumagillol" Bioorg Med Chem Lett. Aug. 1, 2005;15(15):3580-3.
Kawai et al., "Development of Sulfonamide Compounds as Potent Methionine Aminopeptidase Type II Inhibitors with Antiproliferative Properties", Bioorg. Med. Chem. Lett. Jul. 1;16(13):3574-3577 (2006).
Kim et al. "Assessment of the Anti-Obesity Effects of the TNP-470 Analog, CKD-732" J Mol Endocrinol. Apr. 2007;38(4):455-65.
Kim et al. "Development of parenteral formulation for a novel angiogenesis inhibitor, CKD-732 through complexation with hydroxypropyl-beta-cyclodextrin" Int J Pharm. Mar. 19, 2004;272(12):79-89.
Kim et al. "General pharmacology of CKD-732, a new anticancer agent: effects on central nervous, cardiovascular, and respiratory system" Biol Pharm Bull. Feb. 2005;28(2):217-23.
Kim et al., "Depletion of Methionine Aminopeptidase 2 does not Alter Cell Response to Fumagillin or Bengamides," Cancer Res., May 1;64(9):2984-2987 (2004).
Kruger, "TNP-470: An Angiogenesis Inhibitor in Clinical Development for Cancer" Expert Opin Investig Drugs. Jun. 2000;9(6):1383-96.
Lee et al. "Absorption, distribution, metabolism, and excretion of CKD-732, a novel antiangiogenic fumagillin derivative, in rats, mice, and dogs" Arch Pharm Res. Feb. 2004;27(2):265-72.
Lee et al. "Design, Synthesis, and Antiangiogenic Effects of a Series of Potent Novel Fumagillin Analogues" Chem Pharm Bull (Tokyo). Jul. 2007;55(7):1024-9.
Lee et al. "Selective N-demethylation of tertiary aminofumagillols with selenium dioxide via a non-classical Polonovski type reaction" Heterocycles 68(5):915-932, 2006.
Lijnen et al. "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.
Luo et al., "Discovery and Structural Modification of Inhibitors of Methionine Aminopeptidases from *Escherichia coli* and *Saccharomyces cerevisiae*," J. Med. Chem. Jun. 19;46(13):2631-2640 (2003).

Ma et al., "Structural Analysis of Inhibition of *E. coli* Methionine Aminopeptidase: Implication of Loop Adaptability in Selective Inhibition of Bacterial Enzymes," BMC Struct Biol., Dec. 19;7:84 (2007).
Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.
McCowen et al., "Fumagillin (H-3), a New Antibiotic with Amebicidal Properties" Science. Feb. 23, 1951;113(2930):202-3.
Milkowski et al., "TNP-470" Antiangiogenic Agents in Cancer Therapy, Chapter 22 pp. 385-398, 1999.
Miller et al., "Nutritional Phases in Prader-Willi Syndrome," Am. J. Med. Genet. A. 155A(5): 1040-1049 (2011).
Molina et al. "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.
Molina et al. "Fumagillin Treatment of Intestinal Microsporidiosis" N Engl J Med. Jun. 20, 2002;346(25)1963-9.
Molina, et al. "Trial of Oral Fumagillin for the Treatment of Intestinal Microsporidiosis in Patients with HIV Infection" AIDS. Jul. 7, 2000;14(10):1341-8.
Mosteller, R.D., "Simplified Calculation of Body-surface Area," N. Engl .J. Med., 317(17):1098 (Oct. 22, 1987).
Myung et al. "The identification of in vitro metabolites of CKD-732 by liquid chromatography/tandem mass spectrometry" Rapid Commun Mass Spectrom. 2002;16(21):2048-53.
Naganuma et al. "Metronomic doxifluridine chemotherapy combined with the anti-angiogenic agent TNP-470 inhibits the growth of human uterine carcinosarcoma xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very low-calorie diets. National Task Force on the Prevention and Treatment of Obesity, National Institutes of Health" JAMA Aug. 25, 1993;270(8):967-74.
Noel et al. "Increased Risk of Acute Pancreatitis and Biliary Disease Observed in Patients with Type 2 Diabetes"Diabetes Care. May 2009;32(5):834-8. doi: 10.2337/dc08-1755. Epub Feb. 10, 2009.
Pagliarulo et al.,"Gallstone disease and related risk factors in a large cohort of diabetic patients" Dig. Liver Dis., Feb.;36(2):130-134 (2004).
Picoul et al., "Progress in fumagillin synthesis," Pure Appl. Chem. 75(2-3): 235-249 (2003).
Rhee et al., "Angiogenesis inhibitor attenuates parathyroid hormone-induced anabolic effect" Biomed Pharmacother. Jan.;63(1):63-68 (2009).
Rupnick et al., "Adipose Tissue Mass Can be Regulated Through the Vasculature," Proc. Natl. Acad. Sci. U.S.A. Aug. 6;99(16):10730-10735 (2002).
Seneca et al., "Amebiasis: a review. II. Laboratory diagnosis, differential diagnosis and therapy," Am. J. Dig. Dis. Jul.;1(7):310-322 (1956).
Sheppard et al., "3-Amino-2-Hydroxyamides and Related Compounds as Inhibitors of Methionine Aminopeptidase-2", Bioorg. Med. Chem Lett., Feb. 23;14(4):865-868 (2004).
Shin et al., "A Phase I Pharmacokinetic and Pharmacodynamic Study of CKD-732, an Antiangiogenic Agent, in Patients with Refractory Solid Cancer," Invest New Drugs Oct.;28(5):650-658 (2010).
Shin et al., "A Phase lb pharmacokinetic study of the anti-angiogenic agent CKD-732 used in combination with capecitabine and oxaliplatin (XELOX) in metastatic colorectal cancer patients who progressed on irinotecan-based chemotherapy," Invest. New Drugs, Apr.;30(2):672-680 (2012).
Srikumar et al., "Structural insights on Brugia malayi transglutaminase with cinnamoyl derivatives—a molecular docking approach," International Journal of Pharma and Bio Sciences 3(3):998-1006 (2012).
Towbin et al., "Proteomics-based target identification: bengamides as a new class of methionine aminopeptidase inhibitors," J. Biol. Chem. 278(52):52964-52971 (2003).

(56) References Cited

OTHER PUBLICATIONS

Vedantham et al., "Studies towards the synthesis of methionine aminopeptidase inhibitors: diversification utilizing a ROMP-derived coupling reagent", J Comb Chem. Mar.-Apr.;10(2):195-203 (2008).

Wang et al. "Lead optimization of methionine aminopeptidase-2 (MetAP2) inhibitors containing sulfonamides of 5,6-disubstituted anthranilic acids", Bioorg Med Chem Lett. May 15, 2007;17(10):2817-22. Epub Feb. 25, 2007.

Wang et al. "Tumor Suppression by a Rationally Designed Reversible Inhibitor of Methionine Aminopeptidase-2", Cancer Res. 63:7861-7869, 2003.

Wang et al., "Discovery of inhibitors of *Escherichia coli* methionine aminopeptidase with the Fe(II)-form selectivity and antibacterial activity", J Med Chem. Oct. 9, 2008;51(19):6110-20.

Weinsier et al., "Gallstone Formation and Weight Loss" Obes Res. Jan.;1(1):51-56 (1993).

Weinsier et al., "Medically Safe Rate of Weight Loss for the Treatment of Obesity: A Guideline Based on Risk of Gallstone Formation" Am. J. Med. Feb.;98(2):115-117 (1995).

Winter et al., "Endothelial anb3 Integrin-Targeted Fumagillin Nanoparticles Inhibit Angiogenesis in Atherosclerosis," Arterioscler Thromb Vasc. Biol., Sep.;26(9):2103-2109 (2006).

Written Opinion for International Application No. PCT/US2009/066816, mailed Apr. 8, 2010, 3 pages.

Written Opinion for International Application No. PCT/US2011/060127, mailed May 10, 2013, 4 pages.

Written Opinion for International Application No. PCT/US2011/062320, mailed May 29, 2013, 5 pages.

Yanai et al., "Antitumor Activity of a Medium-chain Triglyceride Solution of the Angiogenesis Inhibitor TNP-470 (AGM-1470) when Administered via the Hepatic Artery to Rats Bearing Walker 256 Carcinosarcoma in the Liver," J. Pharmacol. Exp. Ther. Dec.;271(3):1267-1273 (1994).

Yanai et al., "Antitumor Effect of Arterial Administration of a Medium-Chain Triglyceride Solutionof an Angiogenesis Inhibitor, TNP-470, in Rabbits Bearing VX-2 Carcinoma," Pharm Res., May;12(5):653-657 (1995).

Zhang et al., "Angiogenesis Inhibitors Specific for Methionine Aminopeptidase 2 as Drugs for Malaria and Leishmaniasis," J. Biomed. Sci., 9(1):34-40 (Jan.-Feb. 2002).

\* cited by examiner

FUMIGILLOL COMPOUNDS AND METHODS OF MAKING AND USING SAME

CROSS REFERENCE TO RELATED APPLICATIONS

This application claims priority to U.S. Provisional Ser. No. 61/644,612 filed May 9, 2012, hereby incorporated by reference in its entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4 S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitor, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) J Proteome Res 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res 63:7861) and infectious diseases such as microsporidiosis, leishmaniasis, and malaria (Zhang et al. (2002) J Biomed Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc Natl Acad Sci USA 99:10730).

Such MetAP2 inhibitors may be useful as well for patients with excess adiposity and conditions related to adiposity including type 2 diabetes, hepatic steatosis, and cardiovascular disease (via e.g. by ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment.

SUMMARY

The disclosure provides, for example, compounds which may be modulators of MetAP2, and their use as medicinal agents, processes for their preparation, pharmaceutical compositions containing them as an active ingredient both alone or in combination with other agents, to their use as medicaments and to their use in the manufacture of medicaments for the use in the inhibition of MetAP2 activity in warm-blooded animals such as humans. In particular this invention relates to compounds useful for the treatment of obesity, type 2 diabetes, and other obesity-associated conditions. Also provided are pharmaceutical compositions comprising at least one disclosed compound and a pharmaceutically acceptable carrier.

In an embodiment, provided herein are compounds represented by, for example,

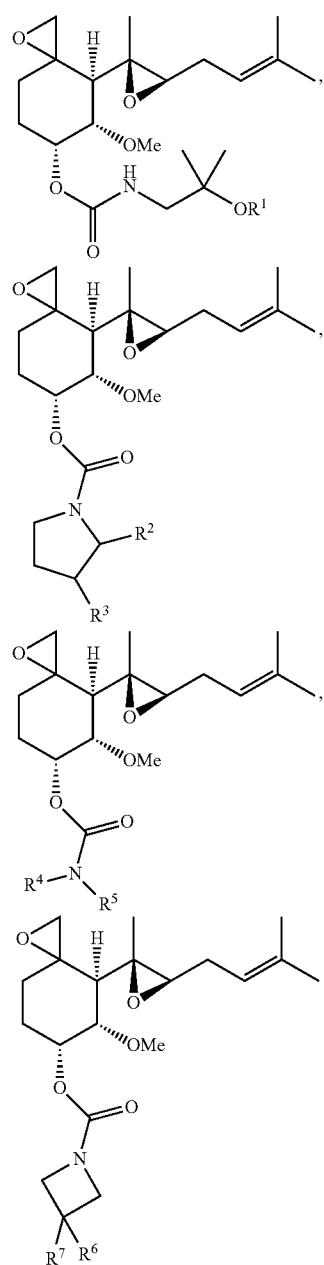

and pharmaceutically acceptable salts, and/or stereoisomers, thereof, wherein $R^1$, $R^2$, $R^3$, $R^4$, $R^5$, $R^6$, and $R^7$ are described herein.

Also provided herein are compounds:

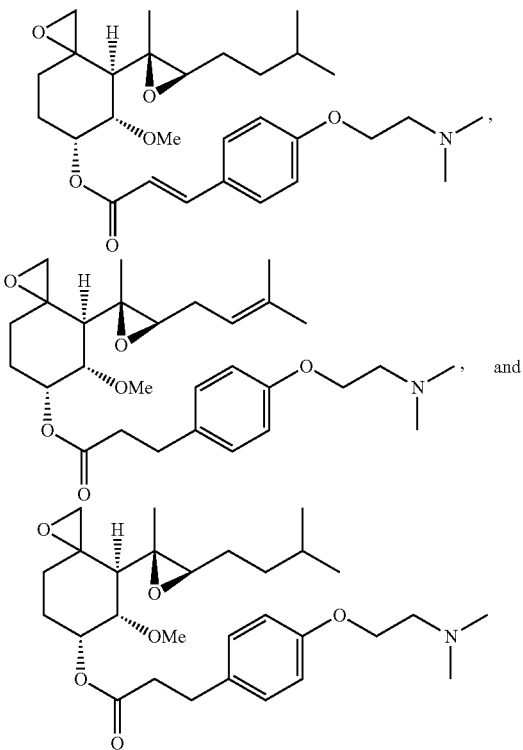

Also provided herein are methods of treating obesity in a patient in need thereof, comprising administering an effective amount of a disclosed compound.

DESCRIPTION OF FIGURES

FIG. 3C indicate that e.g, compound 444 is not available to the testes tissue.

DETAILED DESCRIPTION

Figure 1:
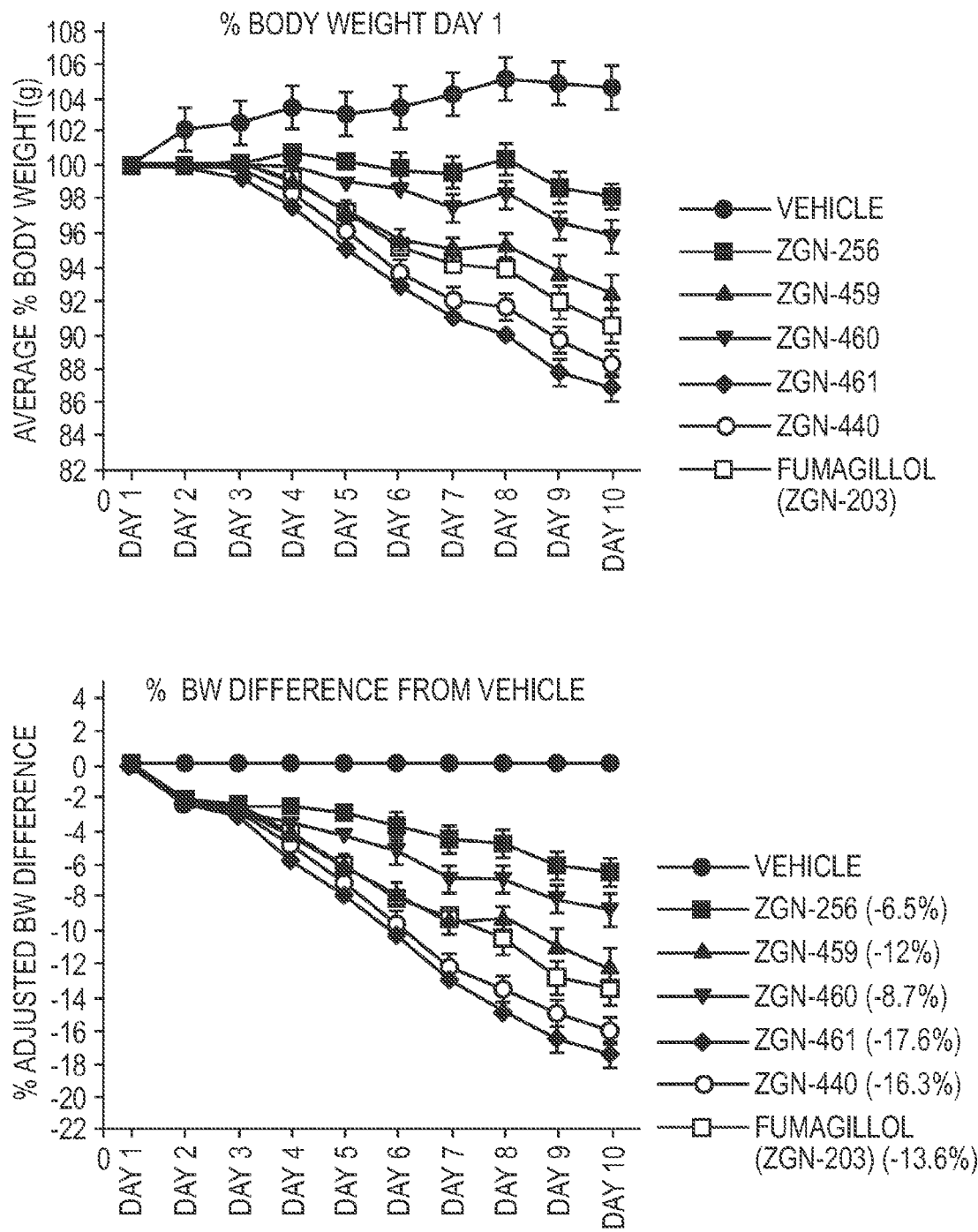
FIG. 1 compares the body weight loss in a mouse model using 0.3 mg/kg subcutaneous dosing of disclosed compounds.

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of obesity, or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. The present invention encompasses various stereoisomers of these compounds and mixtures thereof.

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using steroselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the invention may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence form a contemplated alternative embodiment. Isotopically labeled compounds of the invention can generally be prepared by following procedures analogous to those disclosed in the e.g., Examples herein by substituting an isotopically labeled reagent for a non-isotopically labeled reagent.

In certain embodiments, the present disclosure provides compounds represented by:

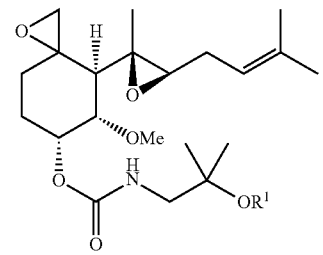

wherein $R^1$ is H or $C_{1-3}$alkyl; or pharmaceutically acceptable salts or stereoisomers thereof. For example, contemplated herein is a compound represented by:

(444)

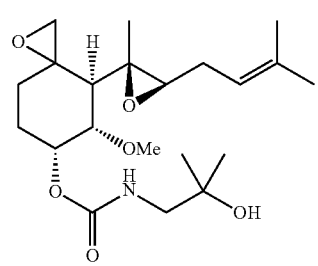

Also provided herein are compounds represented by:

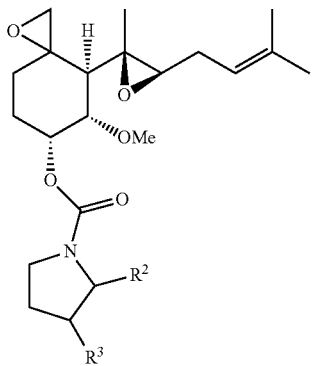

wherein
R² is selected from the group consisting of H, hydroxyl, and C₁₋₄ alkyl (optionally substituted with hydroxyl and/or halo) e.g., isopropyl (optionally substituted with a hydroxyl and/or halo);
R³ is selected from the group consisting of H, and hydroxyl; or pharmaceutically acceptable salts or stereoisomers thereof. In other embodiments, R² may be C₁₋₄ alkyl, optionally substituted with a hydroxyl.

Contemplated herein is a compound represented by:

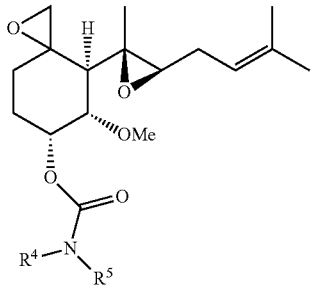

wherein
R⁴ and R⁵ are each methyl; or
R⁴ and R⁵, together with the nitrogen to which they are attached, form a 4-5 membered ring optionally substituted by one or two substituents independently selected from the group consisting of methyl and hydroxyl; or pharmaceutically acceptable salts or stereoisomers thereof. For example, contemplated herein are compounds represented by:

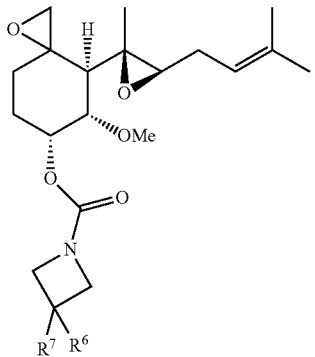

wherein
R⁶ is selected from the group consisting of H, hydroxyl or methyl; and
R⁷ is selected from the group consisting of H, hydroxyl or methyl.

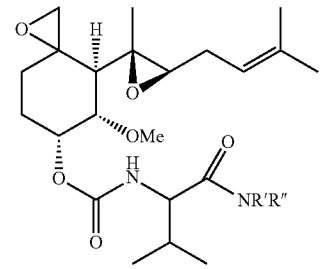

wherein
R' is methyl;
R" is H or methyl; or pharmaceutically acceptable salts or stereoisomers thereof.

Also contemplated herein is a compound represented by:

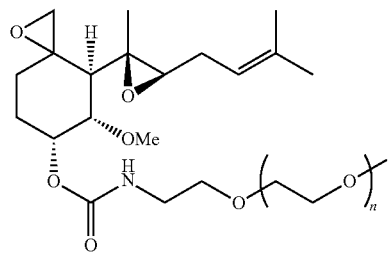

wherein n is 0, 1 or 2; or pharmaceutically acceptable salts or stereoisomers thereof.

In a particular embodiment, contemplated compounds include those selected from the group represented by:

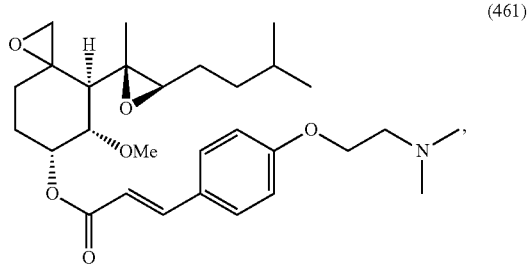

(461)

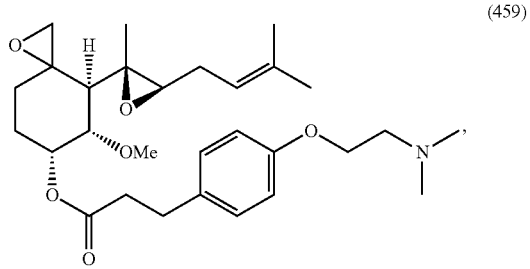

(459)

-continued
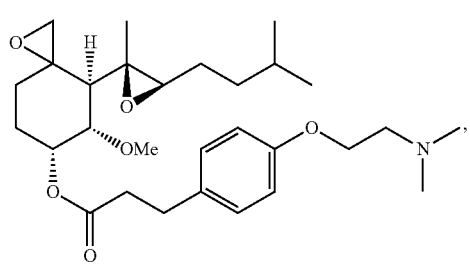
(460)
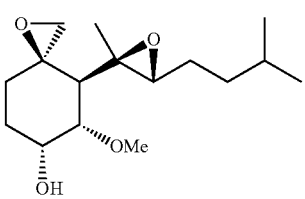
(256)
or pharmaceutically acceptable salts or stereoisomers thereof.
Exemplary compounds include:
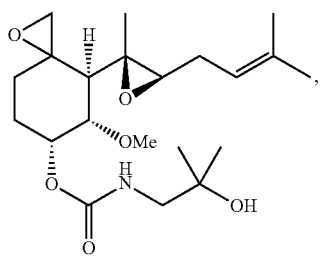,
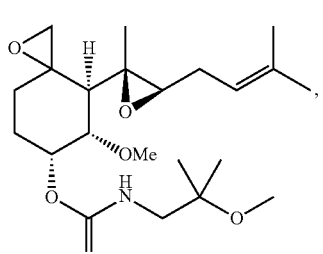,
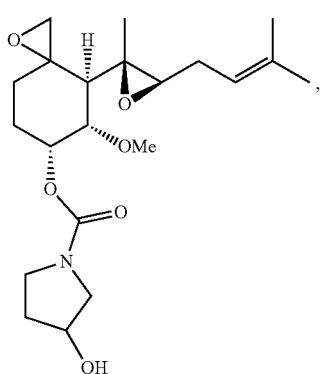,
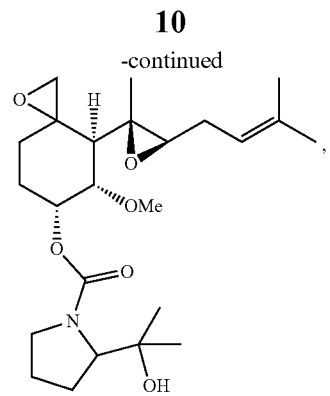,
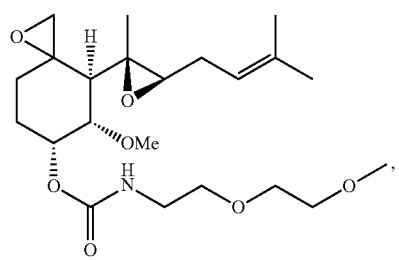,
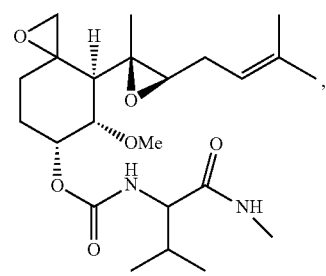,
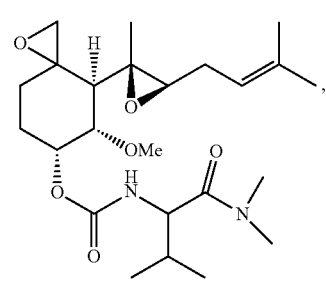,
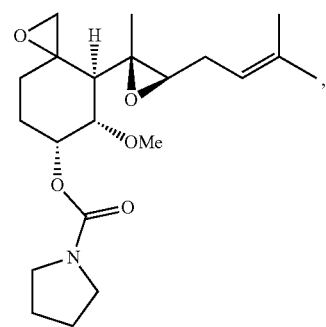,

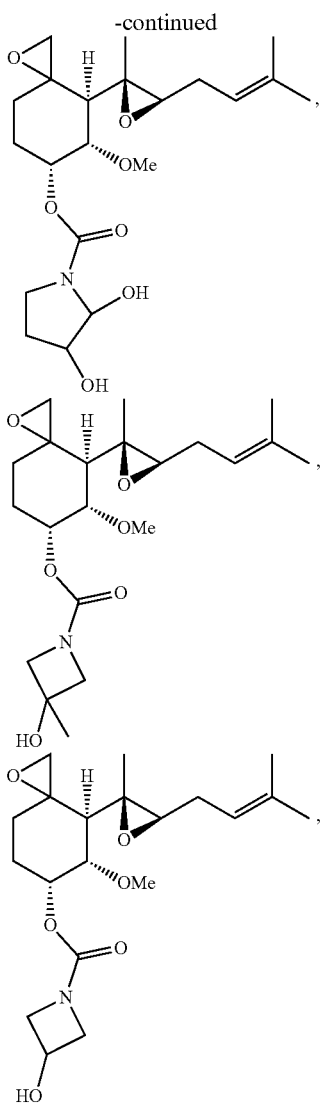

and pharmaceutically salts or stereoisomers thereof.

Another aspect of this disclosure provides methods of modulating the activity of MetAP2. Such methods comprise exposing said receptor to a compound described herein. The ability of compounds described herein to modulate or inhibit MetAP2 can be evaluated by procedures known in the art and/or described herein. Another aspect of the invention provides methods of treating a disease associated with expression or activity of MetAP2 in a patient. For example, a contemplated method includes administering a disclosed compound in an amount sufficient to establish inhibition of intracellular MetAP2 effective to increase thioredoxin production in the patient and to induce multi organ stimulation of anti-obesity processes in the subject, for example, by administering a disclosed compound in an amount insufficient to reduce angiogenesis in the patient.

In certain embodiments, the disclosure provides a method of treating and or ameliorating obesity in a patient by administering an effective amount of a disclosed compound. Also provided herein are methods for inducing weight loss in a patient in need thereof.

Other contemplated methods of treatment include method of treating or amelioriating an obesity-related condition or co-morbidity, by administering a compound disclosed herein to a subject. For example, contemplated herein are methods for treating type 2 diabetes in a patient in need thereof.

Exemplary co-morbidities or other disorders that may be treated by a disclosed compound may include cardiac disorders, endocrine disorders, respiratory disorders, hepatic disorders, skeletal disorders, psychiatric disorders, metabolic disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the disclosure provides a method of treating the above medical indications comprising administering to a subject in need thereof a therapeutically effective amount of a compound described herein.

Obesity or reference to "overweight" refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$(m$^2$) (SI) or 703×weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered considered "obese" at a level differing from the general guidelines, above.

The disclosed compounds may also be useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m$^2$, are also contemplated. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, the disclosure provides methods for treating an overweight or obese subject involving determining a level of at least one biomarker related to being overweight or obese in the subject, and administering an effective amount of a disclosed compound to achieve a target level in the subject. Exemplary biomarkers include body weight, Body Mass Index (BMI), Waist/Hip ratio WHR, plasma adipokines, and a combination of two or more thereof.

In some embodiments, disclosed compounds may not be available to a particular biotissue, which may result in fewer side effects (e.g., resulting in minimal or no involvement of other tissues such as the testes. For example, in some embodiments, compound A, upon administration, may have significantly less concentration in the testes as compared to concentration in the testes of a male patient of other MetAP-2 inhibitors (e g fumigillin (compound (i), or 201), or as compared to fumigillol derivatives such

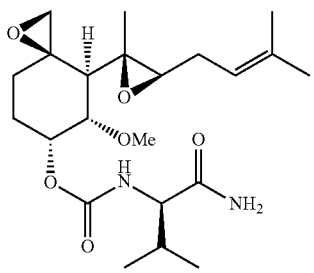

(compound (II), compound (iii)-fumigillol-compound 203, (iv)

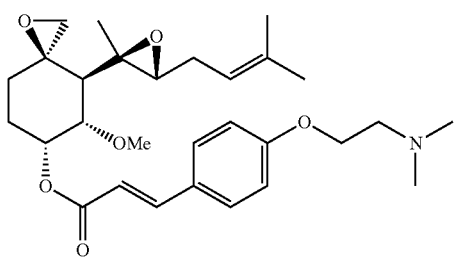 [SMILES: CO[C@@H]1[C@H](OC(=O)/C=C/c2ccc(OCCN(C)C)cc2)CC[C@]2(CO2)[C@H]1[C@@]1(C)O[C@@H]1CC=C(C)C]

(440); or compound 230:

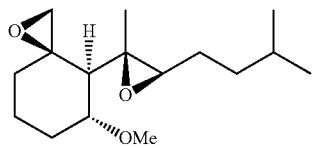

upon administration.

The compounds of the invention may be administered to patients (animals (e.g. cats, dogs, and/or other companion animals or humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. ower dose sufficient to weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HP-MCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleat, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Advantageously, the invention also provides kits for use by a e.g. a consumer in need of weight loss. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol.

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497): 1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9):978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (*Chest* (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4):1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7):824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the invention provides methods for facilitating and maintaining weight loss in a subject involving administering to the subject an amount of a disclosed compound effective to result in weight loss in the subject; and administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

EXAMPLES

Compounds may be identified by number, which may be referred to in some instances with a prefix ZGN.

Example 1

Compound 444

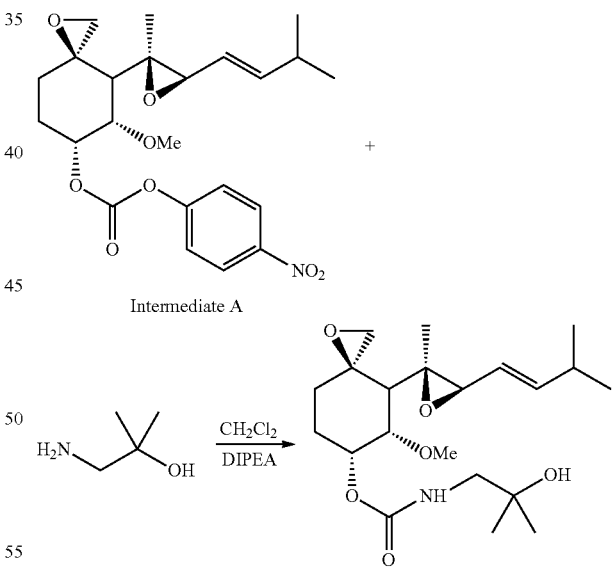

Intermediate A

In a round bottom flask under nitrogen 100 mg (0.23 mmol) of intermediate A was dissolved in 4 mL of $CH_2Cl_2$ and 0.12 g of DIPEA (0.92 mmol) was added followed by 63 mg (0.7 mmol) of 1,1-dimethyl-2-amino ethanol. The mixture was allowed to stir overnight and then condensed in vacuo. The residue was dissolved in 20 mL of EtOAc and washed with 2×20 mL of water, 20 mL of brine, dried over $Na_2SO_4$ and condensed in vacuo. Purification by biotage flash chromatography ($SiO_2$, $MeOH/CH_2Cl_2/Et_3N$ gradient) affords 38 mg of the title compound as a clear viscous oil.

Example 2

Compound 445

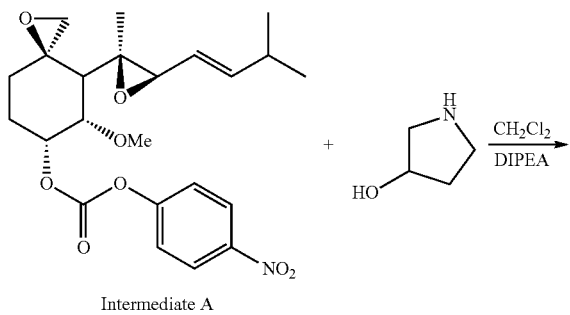

Intermediate A

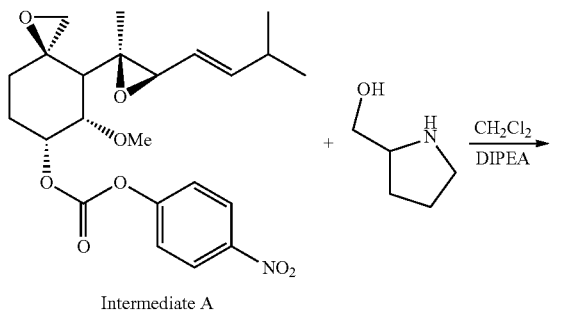

In a round bottom flask under nitrogen 150 mg (0.35 mmol) of intermediate A was dissolved in 5 mL of CH$_2$Cl$_2$ and 0.18 g of DIPEA (1.4 mmol) was added followed by 91 mg (1.05 mmol) of 3-hydroxy pyrrolidine. The mixture was allowed to stir overnight and then condensed in vacuo. The residue was dissolved in 20 mL of EtOAc and washed with 2×20 mL of water, 20 mL of brine, dried over Na$_2$SO$_4$ and condensed in vacuo. Purification by biotage flash chromatography (SiO$_2$, MeOH/CH$_2$Cl$_2$/Et$_3$N gradient) affords 41 mg of the title compound as a clear viscous oil.

Example 3

Compound 446

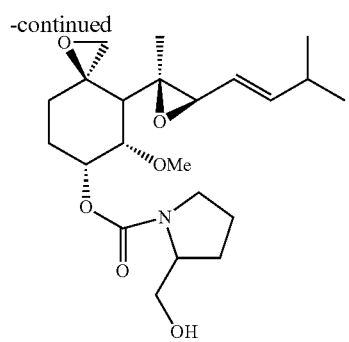

In a round bottom flask under nitrogen 100 mg (0.23 mmol) of intermediate A was dissolved in 4 mL of CH$_2$Cl$_2$ and 0.12 g of DIPEA (0.92 mmol) was added followed by 50 mg (0.7 mmol) of 2-(hydroxymethyl)-pyrrolidine. The mixture was allowed to stir overnight and then condensed in vacuo. The residue was dissolved in 20 mL of EtOAc and washed with 2×20 mL of water, 20 mL of brine, dried over Na$_2$SO$_4$ and condensed in vacuo. Purification by biotage flash chromatography (SiO$_2$, MeOH/CH$_2$Cl$_2$/Et$_3$N gradient) affords 58 mg of the title compound.

Example 4

Compound 447

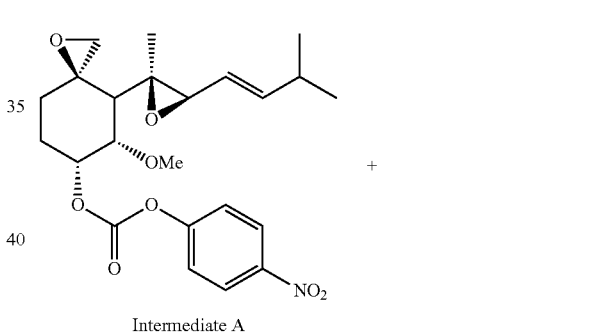

Intermediate A

In a round bottom flask under nitrogen 150 mg (0.35 mmol) of intermediate A was dissolved in 5 mL of CH$_2$Cl$_2$ and 0.18 g of DIPEA (1.4 mmol) was added followed by 136 mg (1.05 mmol) of 3-hydroxy pyrrolidine. The mixture was allowed to stir overnight and then condensed in vacuo. The residue was dissolved in 20 mL of EtOAc and washed with 2×20 mL of water, 20 mL of brine, dried over Na₂SO₄ and condensed in vacuo. Purification by biotage flash chromatography (SiO₂, MeOH/CH₂Cl₂/Et₃N gradient) affords 93 mg of the title compound as a white solid.

Example 5

Compound 448

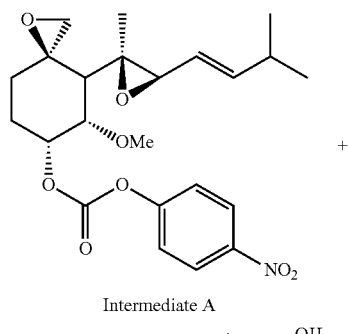

Intermediate A

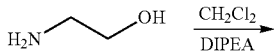

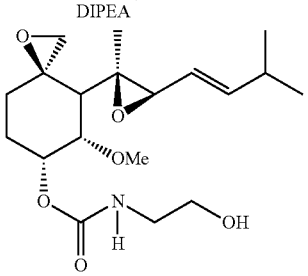

In a round bottom flask under nitrogen 100 mg (0.23 mmol) of intermediate A was dissolved in 4 mL of CH₂Cl₂ and 0.12 g of DIPEA (0.92 mmol) was added followed by 42 ul (0.7 mmol) of 2-hydroxy-ethylamine. The mixture was allowed to stir overnight and then condensed in vacuo. The residue was dissolved in 20 mL of EtOAc and washed with 2×20 mL of water, 20 mL of brine, dried over Na₂SO₄ and condensed in vacuo. Purification by biotage flash chromatography (SiO₂, MeOH/CH₂Cl₂/Et₃N gradient) affords 32 mg of the title compound as a clear oil.

Example 6

Compound 449

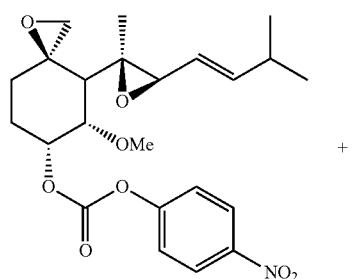

Intermediate A

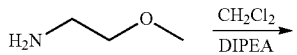
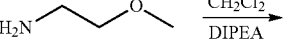

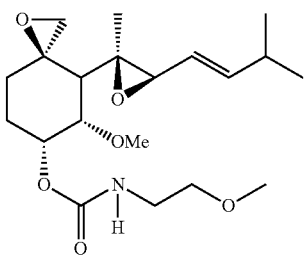

In a round bottom flask under nitrogen 100 mg (0.23 mmol) of intermediate A was dissolved in 4 mL of CH₂Cl₂ and 0.12 g of DIPEA (0.92 mmol) was added followed by 53 ul (0.7 mmol) of 2-methoxy-ethylamine. The mixture was allowed to stir overnight and then condensed in vacuo. The residue was dissolved in 20 mL of EtOAc and washed with 2×20 mL of water, 20 mL of brine, dried over Na₂SO₄ and condensed in vacuo. Purification by biotage flash chromatography (SiO₂, MeOH/CH₂Cl₂/Et₃N gradient) affords 51 mg of the title compound as a clear oil.

Example 7

Compound 450

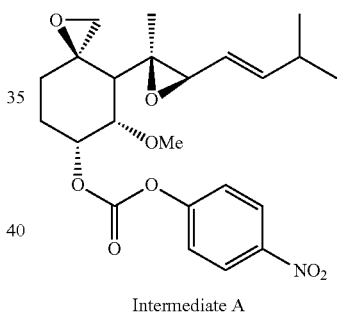

Intermediate A

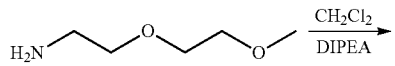

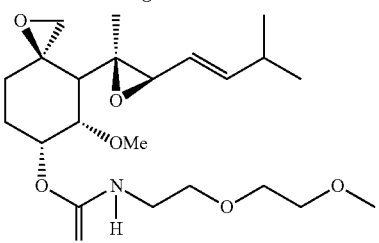

In a round bottom flask under nitrogen 150 mg (0.35 mmol) of intermediate A was dissolved in 5 mL of CH₂Cl₂ and 0.18 g of DIPEA (1.4 mmol) was added followed by 125 mg (1.05 mmol) of 2-(2-Methoxy-ethoxy)-ethylamine. The mixture was allowed to stir overnight and then condensed in vacuo. The residue was dissolved in 20 mL of EtOAc and washed with 2×20 mL of water, 20 mL of brine, dried over Na₂SO₄ and condensed in vacuo. Purification by biotage flash chromatography (SiO₂, MeOH/CH₂Cl₂/Et₃N gradient) affords 99 mg of the title compound as a clear oil

Example 8

Compound 451

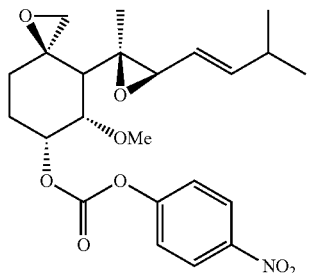

Intermediate A

+

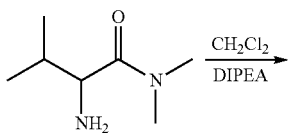

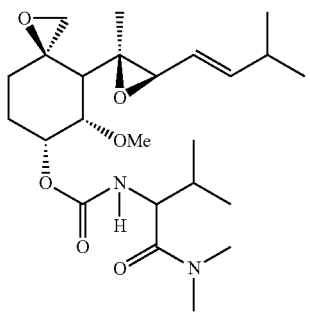

In a round bottom flask under nitrogen 150 mg (0.35 mmol) of intermediate A was dissolved in 5 mL of $CH_2Cl_2$ and 0.18 g of DIPEA (1.4 mmol) was added followed by 150 mg (1.05 mmol) of 2-amino-3-methyl butanoic acid dimethylamide. The mixture was allowed to stir overnight and then condensed in vacuo. The residue was dissolved in 20 mL of EtOAc and washed with 2×20 mL of water, 20 mL of brine, dried over $Na_2SO_4$ and condensed in vacuo. Purification by biotage flash chromatography ($SiO_2$, MeOH/$CH_2Cl_2$/$Et_3N$ gradient) affords 81 mg of the title compound as a clear oil.

Example 9

Compound 452

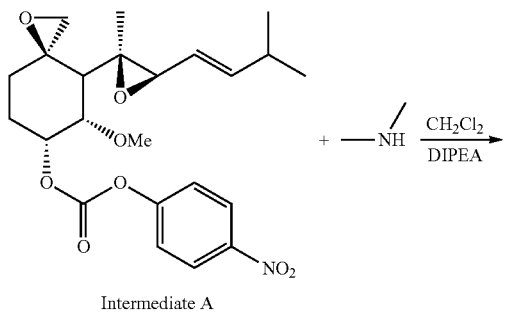

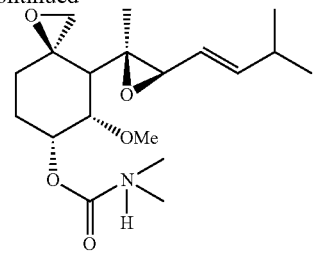

In a round bottom flask under nitrogen 150 mg (0.35 mmol) of intermediate A was dissolved in 5 mL of $CH_2Cl_2$ and 0.18 g of DIPEA (1.4 mmol) was added followed by 0.5 ml (1.05 mmol) of dimethyl amine. The mixture was allowed to stir overnight and then condensed in vacuo. The residue was dissolved in 20 mL of EtOAc and washed with 2×20 mL of water, 20 mL of brine, dried over $Na_2SO_4$ and condensed in vacuo. Purification by biotage flash chromatography ($SiO_2$, MeOH/$CH_2Cl_2$/$Et_3N$ gradient) affords 51 mg of the title compound.

Example 10

Compound 453

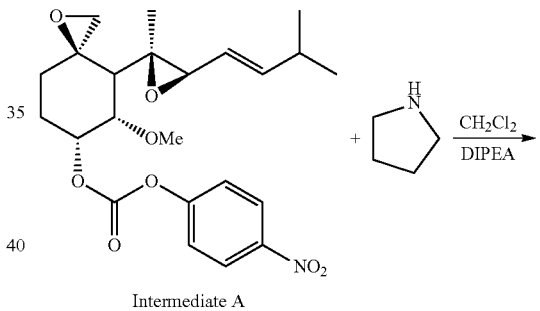

Intermediate A

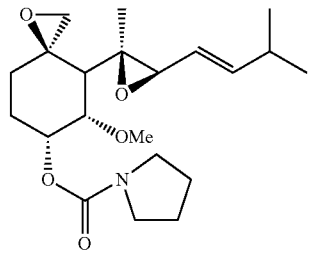

In a round bottom flask under nitrogen 100 mg (0.23 mmol) of intermediate A was dissolved in 4 mL of $CH_2Cl_2$ and 0.12 g of DIPEA (0.92 mmol) was added followed by 50 mg (0.7 mmol) of pyrrolidine. The mixture was allowed to stir overnight and then condensed in vacuo. The residue was dissolved in 20 mL of EtOAc and washed with 2×20 mL of water, 20 mL of brine, dried over $Na_2SO_4$ and condensed in vacuo. Purification by biotage flash chromatography ($SiO_2$, MeOH/$CH_2Cl_2$/$Et_3N$ gradient) affords 62 mg of the title compound as a clear viscous oil.

Example 11

Compound 454

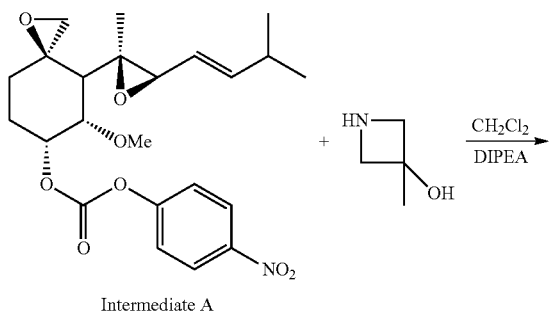

Intermediate A

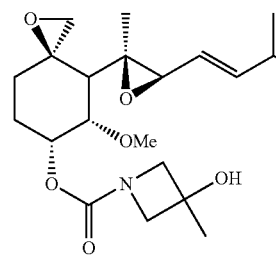

In a round bottom flask under nitrogen 150 mg (0.35 mmol) of intermediate A was dissolved in 5 mL of CH$_2$Cl$_2$ and 0.18 g of DIPEA (1.4 mmol) was added followed by 91 mg (1.05 mmol) of 3-hydroxy-3-methyl azetidine. The mixture was allowed to stir overnight and then condensed in vacuo. The residue was dissolved in 20 mL of EtOAc and washed with 2×20 mL of water, 20 mL of brine, dried over Na$_2$SO$_4$ and condensed in vacuo. Purification by biotage flash chromatography (SiO$_2$, MeOH/CH$_2$Cl$_2$/Et$_3$N gradient) affords 82 mg of the title compound as a clear viscous oil.

Example 12

Compound 455

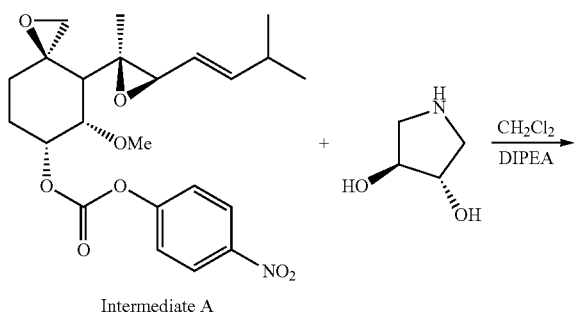

Intermediate A

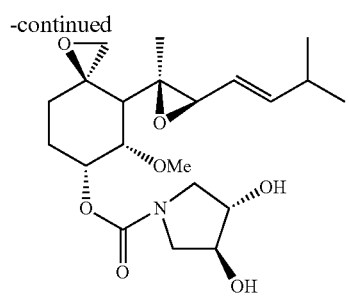

In a round bottom flask under nitrogen 150 mg (0.35 mmol) of intermediate A was dissolved in 5 mL of CH$_2$Cl$_2$ and 0.18 g of DIPEA (1.4 mmol) was added followed by 108 mg (1.05 mmol) of pyrrolidine-3,4-diol. The mixture was allowed to stir overnight and then condensed in vacuo. The residue was dissolved in 20 mL of EtOAc and washed with 2×20 mL of water, 20 mL of brine, dried over Na$_2$SO$_4$ and condensed in vacuo. Purification by biotage flash chromatography (SiO$_2$, MeOH/CH$_2$Cl$_2$/Et$_3$N gradient) affords 43 mg of the title compound as a clear viscous oil.

Example 13

Compound 456

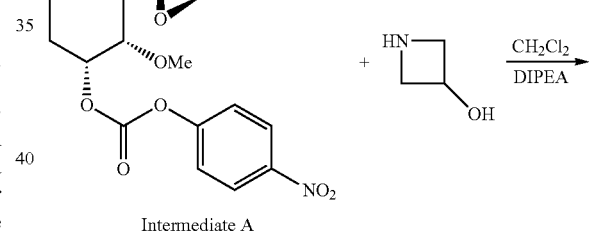

Intermediate A

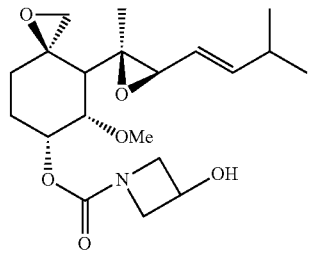

In a round bottom flask under nitrogen 150 mg (0.35 mmol) of intermediate A was dissolved in 5 mL of CH$_2$Cl$_2$ and 0.18 g of DIPEA (1.4 mmol) was added followed by 110 mg (1.05 mmol) of 3-hydroxy azetidine. The mixture was allowed to stir overnight and then condensed in vacuo. The residue was dissolved in 20 mL of EtOAc and washed with 2×20 mL of water, 20 mL of brine, dried over Na$_2$SO$_4$ and condensed in vacuo. Purification by biotage flash chromatography (SiO$_2$, MeOH/CH$_2$Cl$_2$/Et$_3$N gradient) affords 43 mg of the title compound as a clear viscous oil.

Example 14

Compound 457

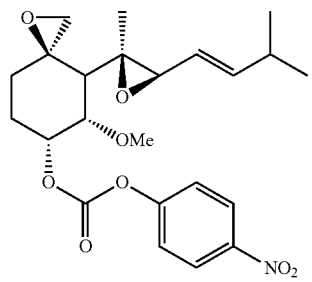

Intermediate A

+

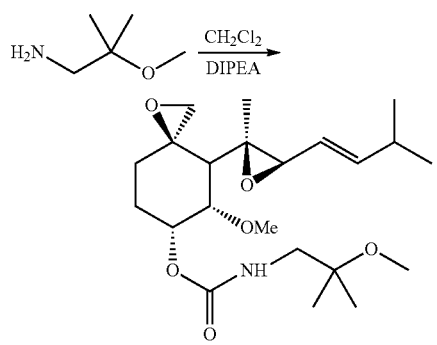

In a round bottom flask under nitrogen 100 mg (0.23 mmol) of intermediate A was dissolved in 4 mL of CH$_2$Cl$_2$ and 0.12 g of DIPEA (0.92 mmol) was added followed by 108 mg (0.7 mmol) of 2-Methoxy-2-methyl-propylamine. The mixture was allowed to stir overnight and then condensed in vacuo. The residue was dissolved in 20 mL of EtOAc and washed with 2×20 mL of water, 20 mL of brine, dried over Na$_2$SO$_4$ and condensed in vacuo. Purification by biotage flash chromatography (SiO$_2$, MeOH/CH$_2$Cl$_2$/Et$_3$N gradient) affords 71 mg of the title compound as a clear viscous oil.

Example 15

Compound 258

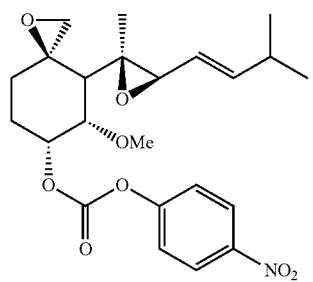

Intermediate A

+

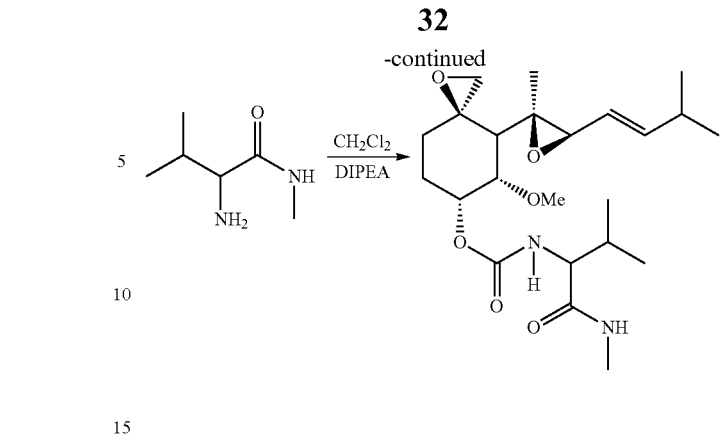

In a round bottom flask under nitrogen 150 mg (0.35 mmol) of intermediate A was dissolved in 5 mL of CH$_2$Cl$_2$ and 0.18 g of DIPEA (1.4 mmol) was added followed by 170 mg (1.05 mmol) of 2-amino-3-methyl butanoic acid methylamide. The mixture was allowed to stir overnight and then condensed in vacuo. The residue was dissolved in 20 mL of EtOAc and washed with 2×20 mL of water, 20 mL of brine, dried over Na$_2$SO$_4$ and condensed in vacuo. Purification by biotage flash chromatography (SiO$_2$, MeOH/CH$_2$Cl$_2$/Et$_3$N gradient) affords 33 mg of the title compound as a clear oil.

Example 16

Compound 256

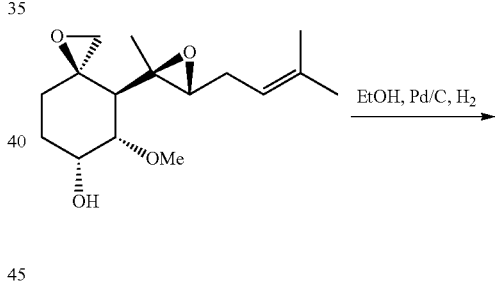

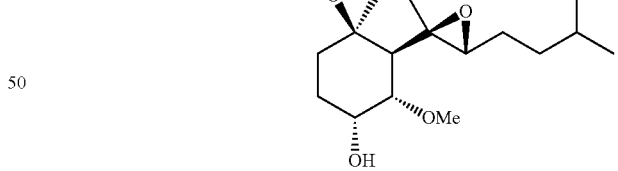

1 g (3.5 mmol) of the fumagillol is dissolved in 15 ml of ethanol and 380 mg (0.35 mmol) of Pd/C is added. The flask is capped and evacuated and back filled with nitrogen three times. Then the flask is evacuated and backfilled with hydrogen. The mixture is stirred at room temperature for 1 h. After the reaction is complete the flask is evacuated and backfilled with nitrogen three tomes and then the Pd/C is removed by filtration through Celite. The solvents are removed in vacuo to give 800 mg (81%) of the desired product

Example 17

Compound 459

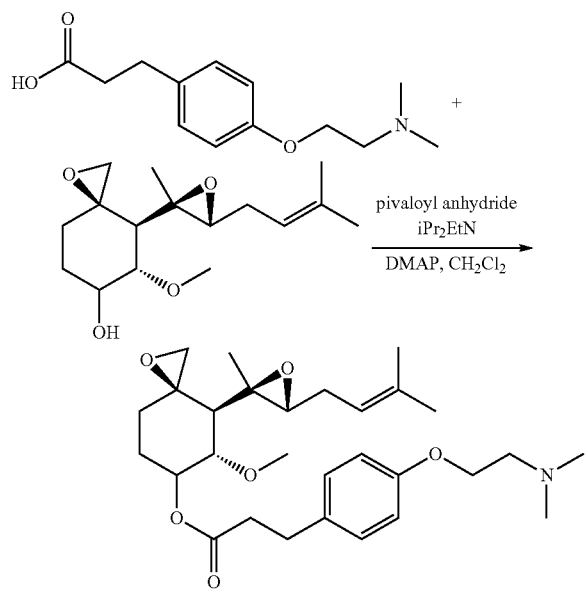

In a round bottom flask under nitrogen 280 mg (1 mmol) of fumagillol, 270 mg (1.16 mmol) of the cinnamic acid derivative, 13.4 mg (0.11 mmol) of DMAP, and 0.22 mL (1.3 mmol) of dissopropyl ethyl amine is dissolved in 10 ml of hexanes. To the stirred solution is added 0.22 ml (1.16 mmol) of pivaloyl anhydride. The reaction is allowed to stir at room temp for 6 h at which point an additional 0.22 ml (1.16 mmol) of pivaloyl anhydride is added. The reaction is allowed to stir over night and the next day the reaction is diluted with ethyl acetate (50 ml) and washed with saturated sodium bicarbonate (20 ml) and dried over sodium sulfate. Purification by flash chromatography (biotage, SiO$_2$, Methanol/dichloromethane gradient) gives 278 mg of the title compound (55% yield).

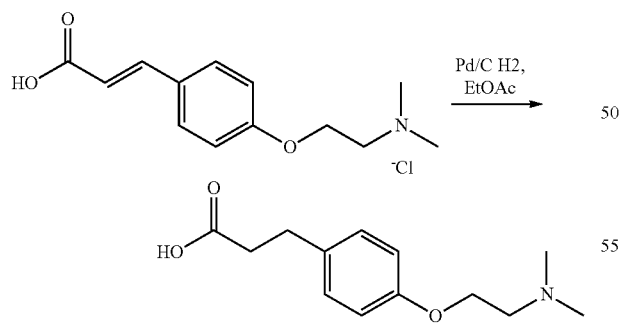

200 mg (0.85 mmol) of the unsaturated cinnamic acid derivative is dissolved in 5 ml of ethyl acetate and 9 mg (0.085 mmol) of Pd/C is added. The flask is capped and evacuated and back filled with nitrogen three times. Then the flask is evacuated and backfilled with hydrogen. The mixture is stirred at room temperature for 18 h. After the reaction is complete the flask is evacuated and backfilled with nitrogen three tomes and then the Pd/C is removed by filtration through Celite. The solvents are removed in vacuo to give 165 mg (81%) of the desired product

Example 17

Compound 460

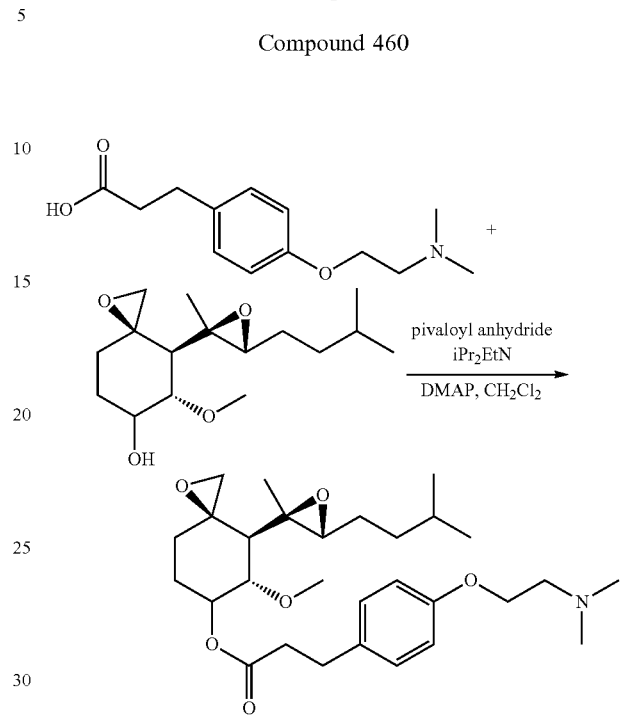

In a round bottom flask under nitrogen 286 mg (1 mmol) of Compound 256 (ZGN-256), 270 mg (1.16 mmol) of the cinnamic acid derivative, 13.4 mg (0.11 mmol) of DMAP, and 0.22 mL (1.3 mmol) of dissopropyl ethyl amine is dissolved in 10 ml of hexanes. To the stirred solution is added 0.22 ml (1.16 mmol) of pivaloyl anhydride. The reaction is allowed to stir at room temp for 6 h at which point an additional 0.22 ml (1.16 mmol) of pivaloyl anhydride is added. The reaction is allowed to stir over night and the next day the reaction is diluted with ethyl acetate (50 ml) and washed with saturated sodium bicarbonate (20 ml) and dried over sodium sulfate. Purification by flash chromatography (biotage, SiO$_2$, Methanol/dichloromethane gradient) gives 293 mg of the title compound (58% yield).

Example 18

Compound 461

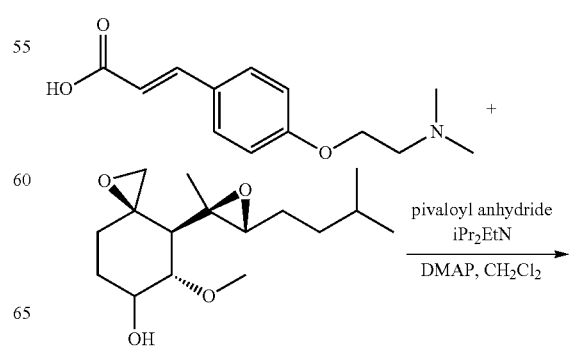

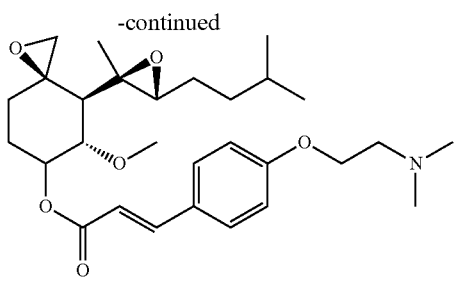

In a round bottom flask under nitrogen 200 mg (0.7 mmol) of compound 256, 160 mg (0.7 mmol) of the cinnamic acid derivative, 9.3 mg (0.07 mmol) of DMAP, and 0.16 mL (0.91 mmol) of dissopropyl ethyl amine is dissolved in 10 ml of heptane. To the stirred solution is added 0.14 ml (0.7 mmol) of pivaloyl anhydride. The reaction is allowed to stir over night and the next day the reaction is diluted with ethyl acetate (50 ml) and washed with saturated sodium bicarbonate (20 ml) and dried over sodium sulfate. Purification by flash chromatography (biotage, $SiO_2$, Methanol/dichloromethane gradient) gives 90 mg of the title compound (24% yield).

Example 19

Studies were conducted using 18-20 week old Diet Induced Obese (DIO) C57BL/6 mice. The study was a 7 day screen that included 18-20 week old C57BL/6 mice that were provided a high fat diet for 14 weeks, and treated with compounds injected subcutaneously daily at 0.3 mg/kg. FIG. 1 shows the weight loss of effect of this dose for various disclosed compounds.

Example 20

Figure 2A:
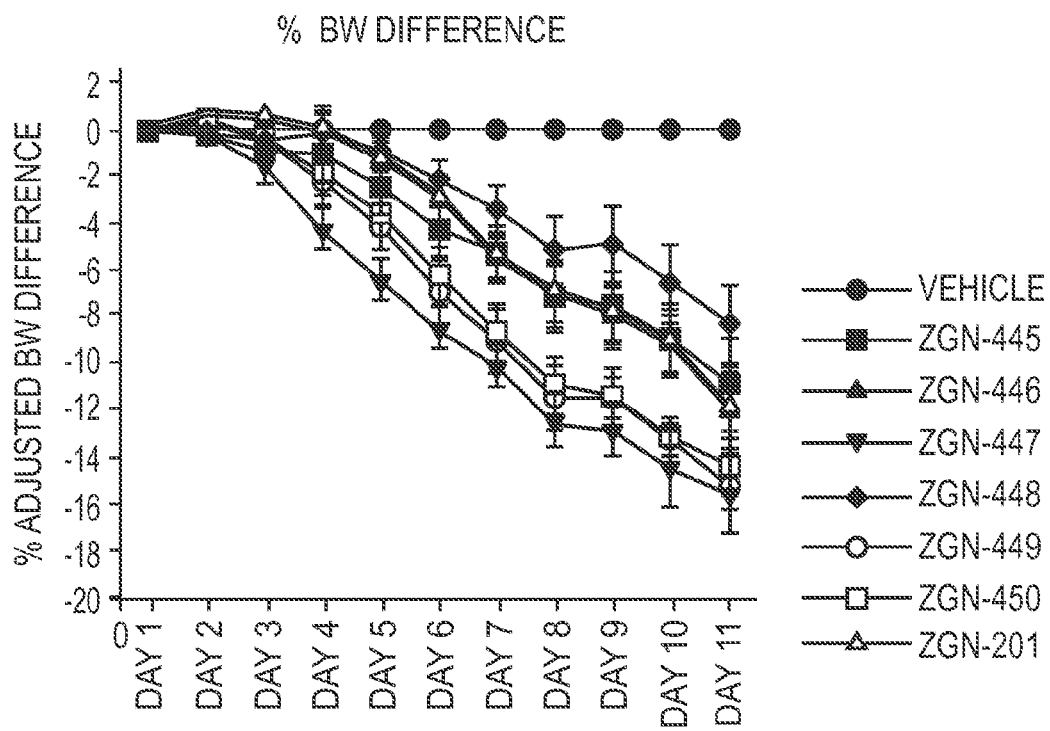
FIGS. 2A, 2B, and 2C compares the body weight loss in a mouse model using e.g., 3 mg/kg oral dosing of disclosed compounds.
Figure 2B:
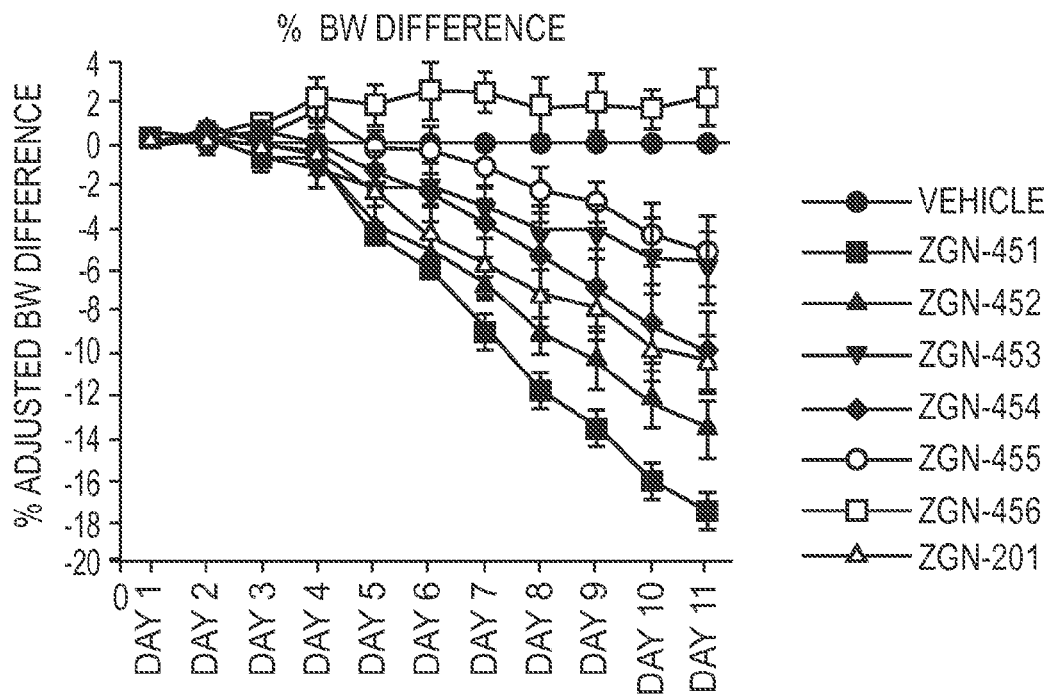
Figure 2C:
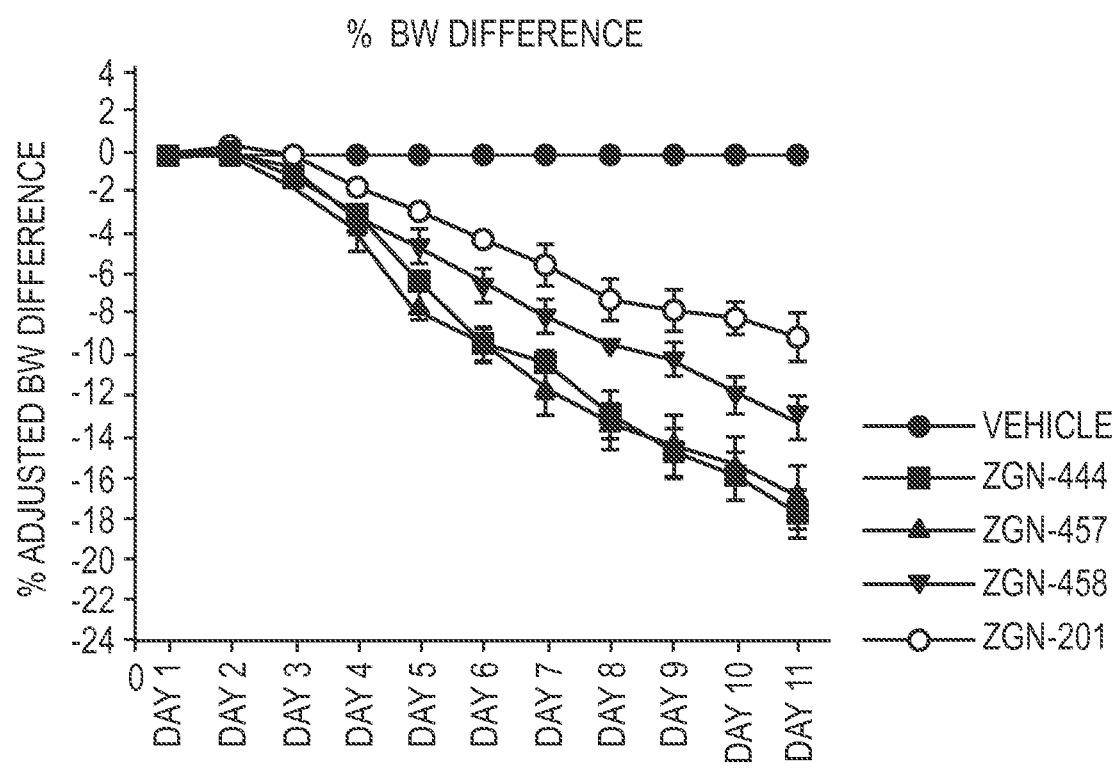

10 day studies were conducted that included 20 week old C57BL/6 mice on high fat diet for 14 weeks treated with either 10% DMSO or the same vehicle containing an amount of drug to deliver a dose of 3 mg/kg PO (oral gavage) of disclosed compounds for 10 days. ZGN-201 control was dosed at 1 mg/kg PO. ZGN-444 was dosed at both 3 mg/kg and 0.3 mg/kg. FIG. 2A, B, C depicts the 10-day PO efficacy at 3 mg/kg of disclosed compound. FIG. 2C shows 10-day PO efficicacy at 3 mg/kg for compound 444 and other disclosed compounds, indicating the oral efficacy of compound 444.

Figure 3A:
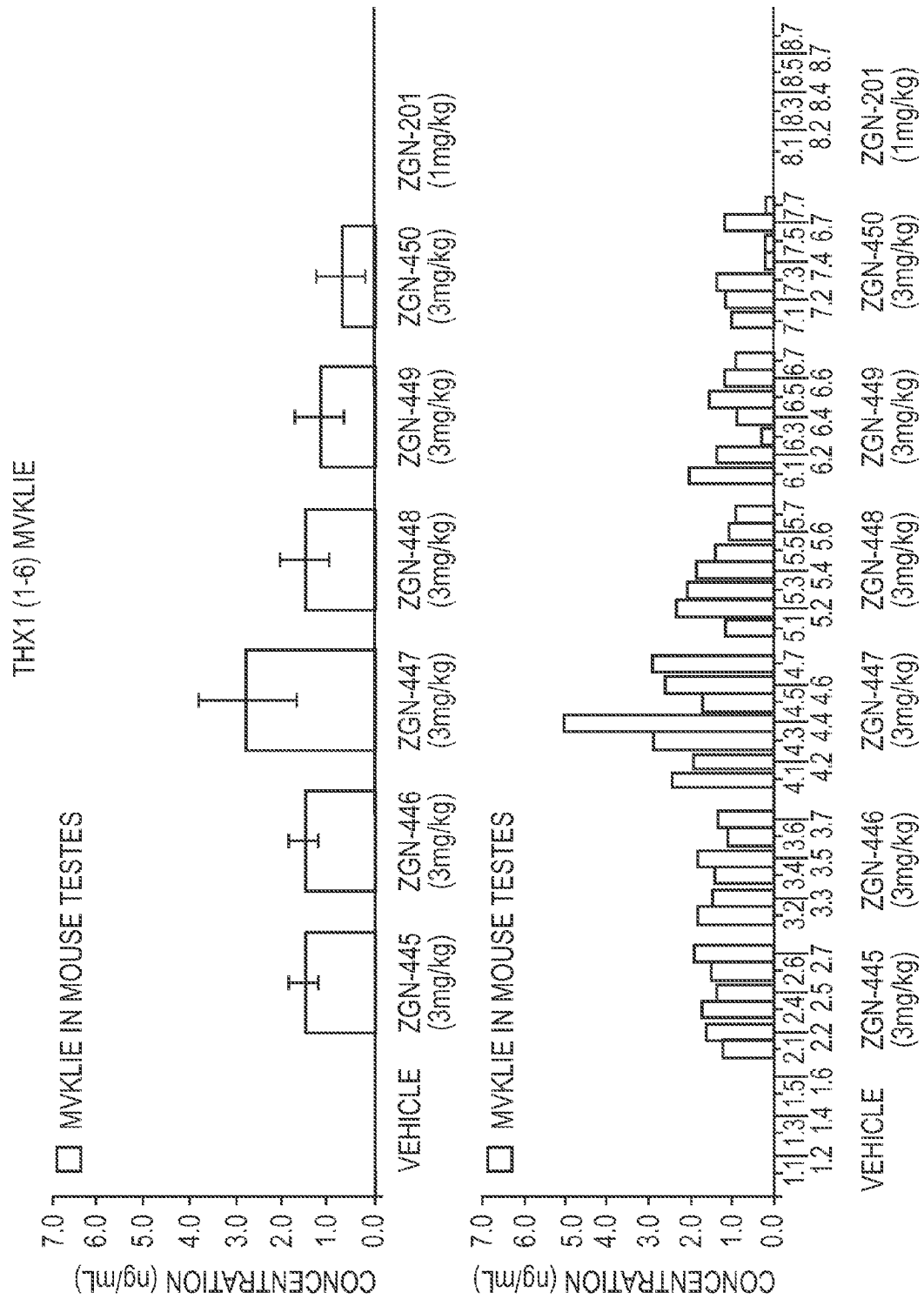
FIGS. 3A, 3B, 3C depict the concentration of a testes biomarker after administration of compounds in the mouse model of FIG. 2 and indicates the availability or non-availability of the tested compounds to the testes tissue.
Figure 3B:
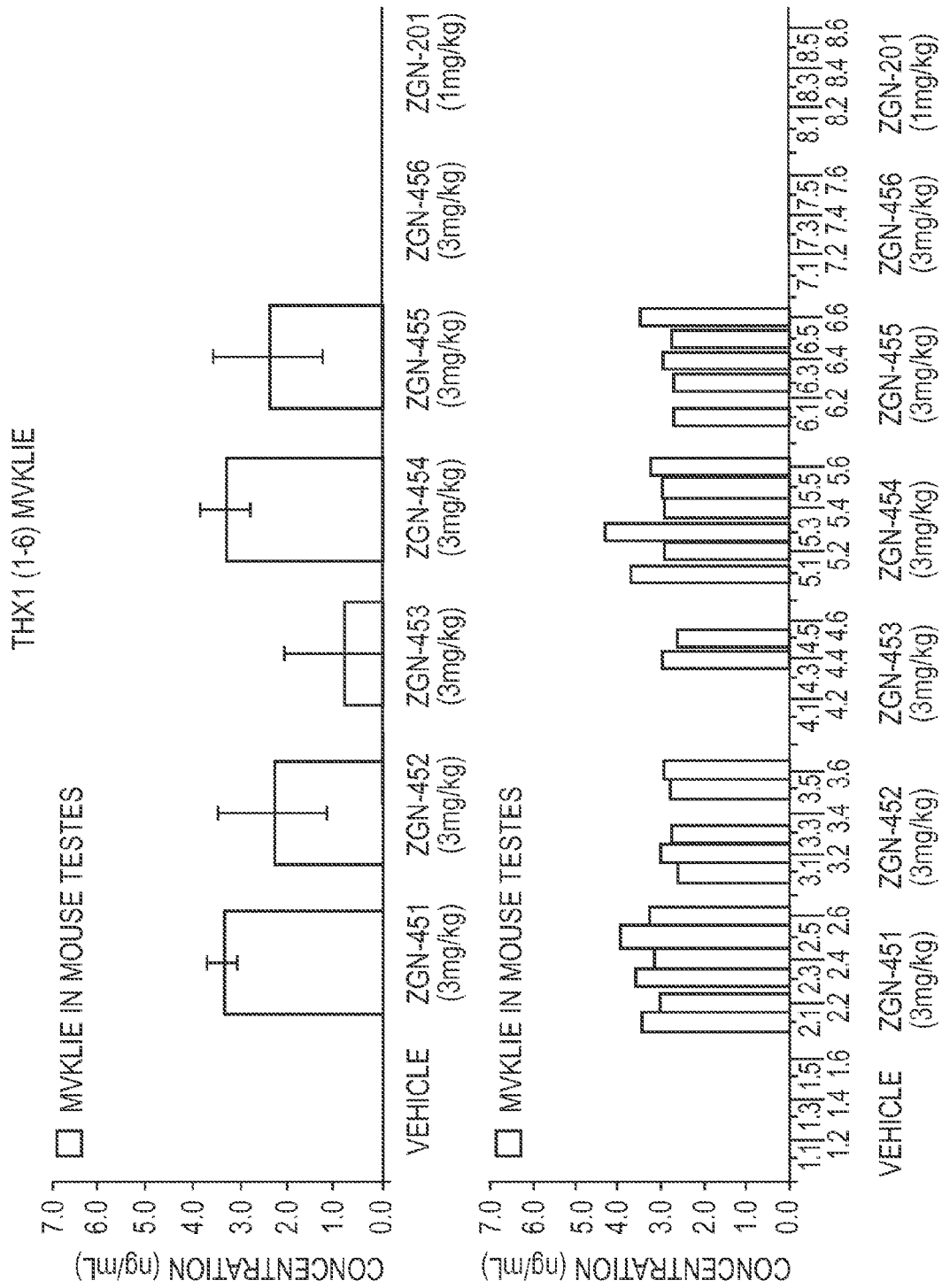
Figure 3C:
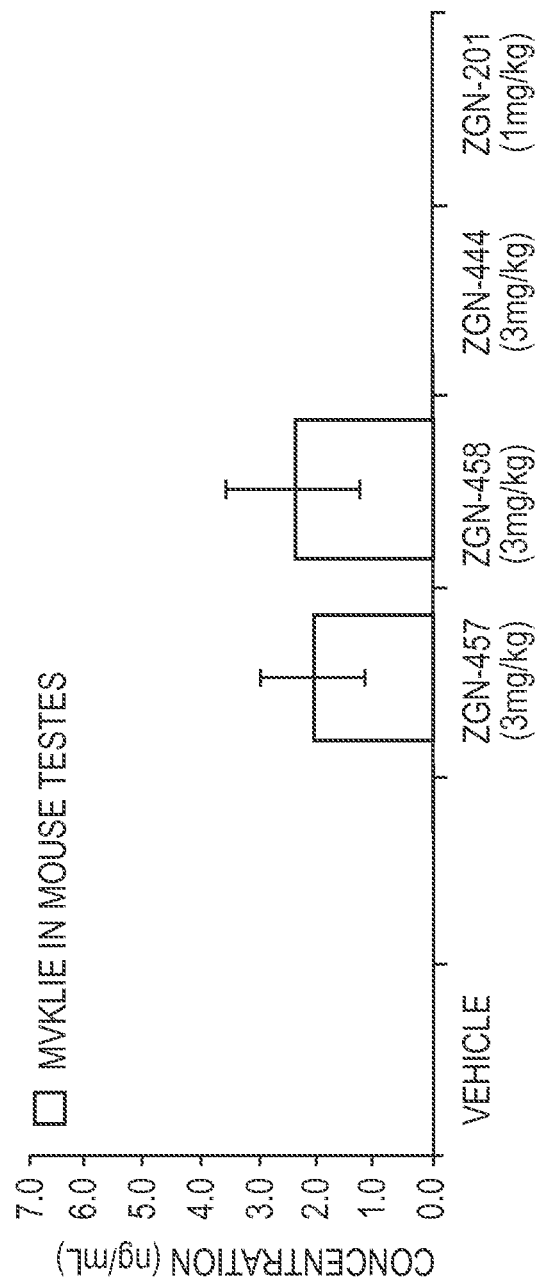

At the end of these studies testes from the mice were harvested, homogenized and digested with endoproteinase Glu-C. The N-terminal peptide of mouse thioredoxin (a selective substrate of the target enzyme MetAP2 was analyzed by LC-MS/MS for full length peptide amino acid 1-6 (SEQ ID NO. 1: MVKLIE), and the degree of detection in a given tissue is indicative of MetAP2 inhibition in that tissue. (See J Proteome Res. 2008; 7:4807). FIGS. 3A, B, and C, show the concentration of SEQ ID NO. 1 (ng/mL) and indicates that certain compounds are not available to the testes tissue as compared to the other tested compounds (and therefore may have fewer testes related side effects). FIG. 3C indicates compound 444 administered orally is not available to the testes tissue.

Incorporation By Reference

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

We claim:

1. A compound represented by

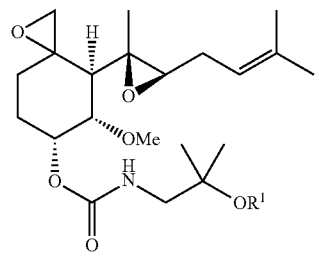

wherein $R^1$ is H or $C_{1-3}$alkyl; or pharmaceutically acceptable salts or stereoisomers thereof.

2. The compound of claim 1, represented by:

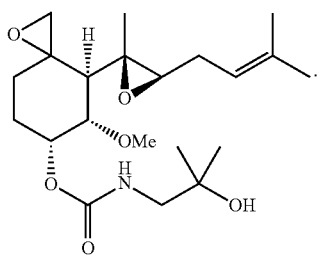 [SMILES: CO[C@@H]1[C@H](OC(=O)NCC(C)(C)O)CCC2(CO2)[C@H]1[C@@]1(C)O[C@@H]1CC=C(C)C]

3. A compound represented by:

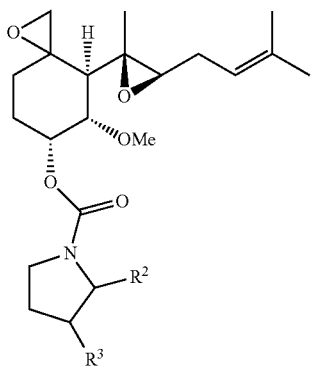

wherein
R² is selected from the group consisting of hydroxyl and isopropyl (optionally substituted with a hydroxyl);
R³ is selected from the group consisting of H, and hydroxyl; or pharmaceutically acceptable salts or stereoisomers thereof.

4. A compound represented by:

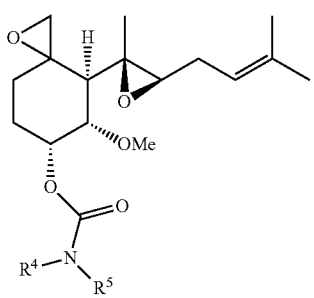

wherein
R⁴ and R⁵, together with the nitrogen to which they are attached, form a 4 membered ring optionally substituted by one or two substituents independently selected from the group consisting of methyl and hydroxyl;
or pharmaceutically acceptable salts or stereoisomers thereof.

5. The compound of claim 4, represented by:

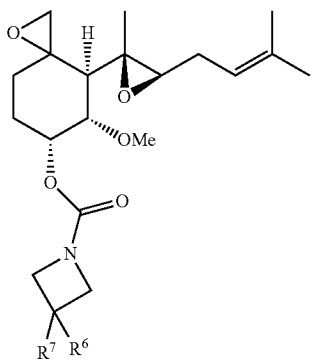

wherein
R⁶ is selected from the group consisting of H, hydroxyl and methyl; and

R⁷ is selected from the group consisting of H, hydroxyl and methyl.

6. A compound represented by

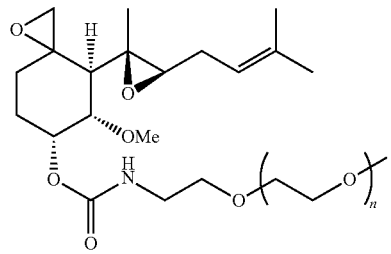

wherein
n is 1 or 2; or pharmaceutically acceptable salts or stereoisomers thereof.

7. A compound selected from the group consisting of:

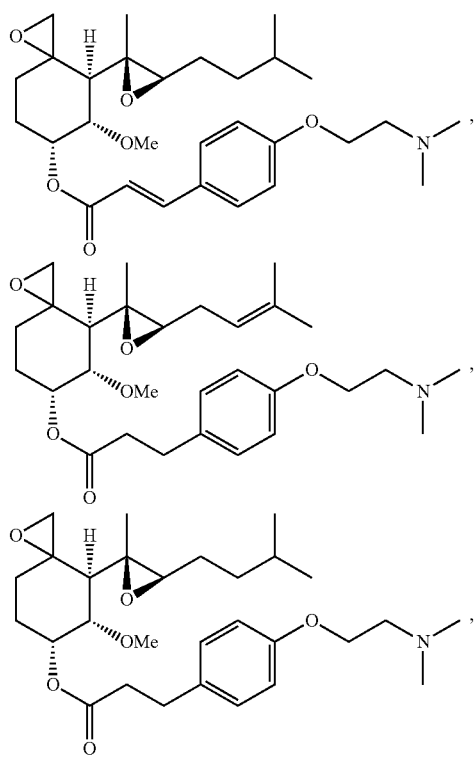

and pharmaceutically acceptable salts or stereoisomers thereof.

8. A compound selected from the group consisting of:

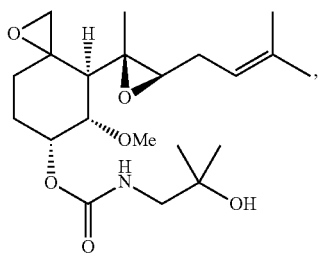

-continued

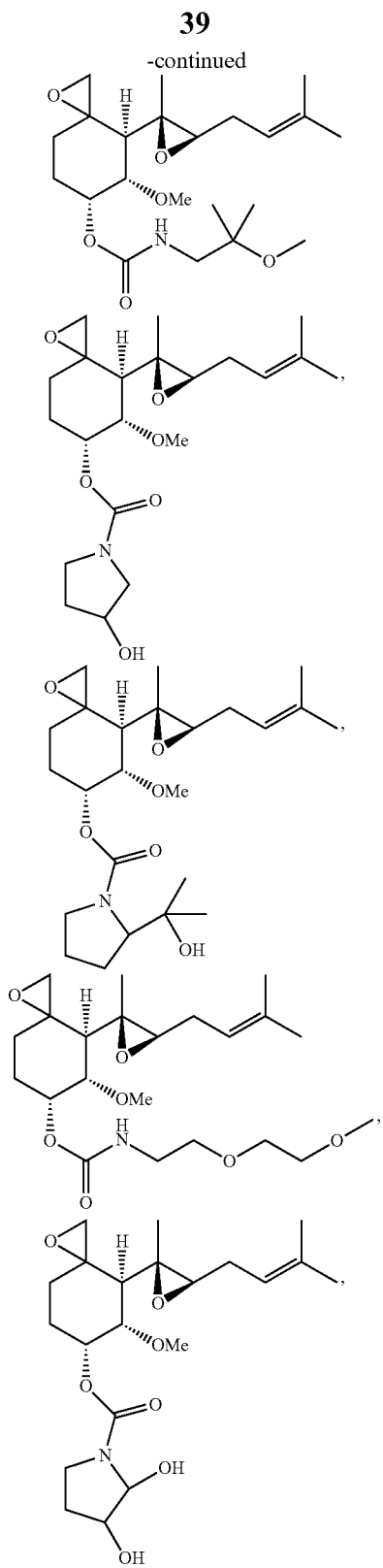

-continued

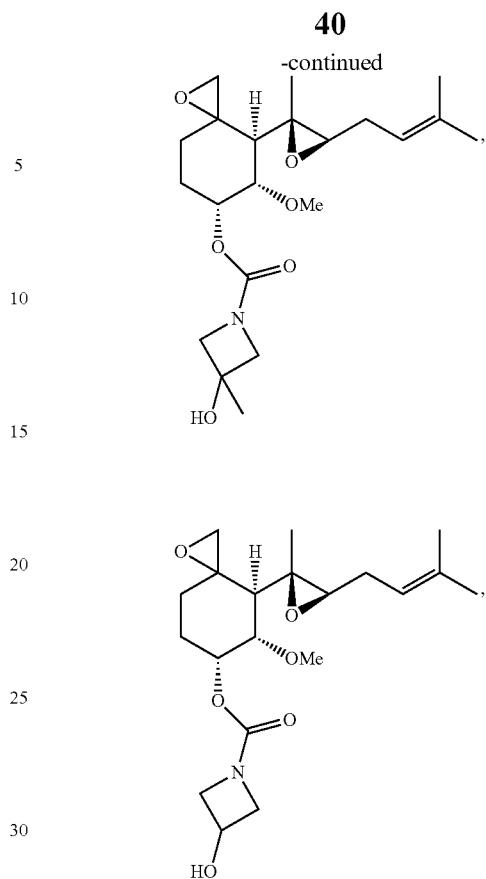

and pharmaceutically salts or stereoisomers thereof.

9. A method of treating and/or controlling obesity, comprising administering to a patient in need thereof an effective amount of the compound of claim 1.

10. A method of inducing weight loss in a patient in need thereof, comprising administering to said patient an effective amount of the compound of claim 1.

11. The method of claim 9, wherein the patient is a human.

12. The method of claim 9, wherein the patient has a body mass index greater than or equal to about 25 kg/m² before the administration.

13. The method claim 9, wherein the compound is administered orally, intravenously, or subcutaneously.

14. The method of claim 9, wherein the compound is administered orally.

15. A pharmaceutical composition comprising the compound of claim 1, and a pharmaceutically acceptable carrier.

16. The composition of claim 15, wherein the composition is formulated as a unit dose.

17. The method of claim 9, wherein the administering comprises administering said compound in an amount insufficient to reduce angiogenesis in the patient.

\* \* \* \* \*